United States Patent
Lim et al.

(10) Patent No.: US 11,827,679 B2
(45) Date of Patent: Nov. 28, 2023

(54) SELF-ASSEMBLED NANOSTRUCTURES OF ELASTIN- AND RESILIN-BASED BLOCK COPOLYPEPTIDES WITH STIMULI RESPONSIVENESS AND RESILIENCE FOR DRUG DELIVERY SYSTEM, TISSUE ENGINEERING AND REGENERATIVE MEDICINE AND METHODS OF PREPARING THE SAME

(71) Applicant: Industry-University Cooperation Foundation Hanyang University Erica Campus, Ansan-si (KR)

(72) Inventors: Dong Woo Lim, Ansan-si (KR); Aamna Basheer, Ansan-si (KR); Jae Sang Lee, Ansan-si (KR); Min Jung Kang, Bucheon-si (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 953 days.

(21) Appl. No.: 16/087,774

(22) PCT Filed: Mar. 23, 2017

(86) PCT No.: PCT/KR2017/003113
§ 371 (c)(1),
(2) Date: Sep. 24, 2018

(87) PCT Pub. No.: WO2017/164661
PCT Pub. Date: Sep. 28, 2017

(65) Prior Publication Data
US 2020/0354416 A1 Nov. 12, 2020

(30) Foreign Application Priority Data
Mar. 23, 2016 (KR) .................. 10-2016-0034372

(51) Int. Cl.
| | |
|---|---|
| *A61K 38/39* | (2006.01) |
| *C07K 14/78* | (2006.01) |
| *C07K 14/435* | (2006.01) |
| *A61K 47/42* | (2017.01) |
| *A61L 27/22* | (2006.01) |
| *C08J 3/075* | (2006.01) |

(52) U.S. Cl.
CPC ........ *C07K 14/43563* (2013.01); *A61K 38/39* (2013.01); *A61K 47/42* (2013.01); *A61L 27/227* (2013.01); *C07K 14/78* (2013.01); *C08J 3/075* (2013.01); *C08J 2389/00* (2013.01)

(58) Field of Classification Search
CPC ..... C07K 14/78; C07K 2319/00; A61K 38/00
See application file for complete search history.

(56) References Cited

U.S. PATENT DOCUMENTS

| | | |
|---|---|---|
| 2015/0112022 A1 | 4/2015 | Chilkoti et al. |
| 2016/0068578 A1 | 3/2016 | Demirel et al. |

FOREIGN PATENT DOCUMENTS

| | | | |
|---|---|---|---|
| JP | 2007-531506 A | 11/2007 | |
| WO | WO 2015/116665 A2 | 8/2015 | |
| WO | WO-2015116665 A2 * | 8/2015 | ............. C07K 1/047 |

OTHER PUBLICATIONS

Prhashanna et al., Biomacromolecules, 2019, vol. 20:1178-1189.*
Dutta, Naba K. et al., "A Genetically Engineered Protein Responsive to Multiple Stimuli** ", *Angewandte Chemie International Edition*, vol. 50, 2011 (pp. 4428-4431).
International Search Report dated Jun. 26, 2017 in corresponding International Patent Application No. PCT/KR2017/003113 (2 pages in English and 2 pages in Korean).

* cited by examiner

*Primary Examiner* — Xiaozhen Xie
(74) *Attorney, Agent, or Firm* — NSIP Law

(57) ABSTRACT

The present disclosure relates to a self-assembled nanostructure of an elastin- and resilin-based block copolypeptide with stimuli responsiveness and resilience for drug delivery, tissue engineering and regenerative medicine, a method for preparing the same and application thereof. The diblock polypeptide reversibly forms a self-assembled micelle structure in response to temperature stimuli and a hydrogel prepared using the triblock polypeptide undergoes reversible sol-gel or gel-sol transition in response to temperature stimuli and exhibits enhanced mechanical strength due to chemical crosslinkages between tyrosine residues. With such superior properties, the diblock/triblock polypeptide of the present disclosure can be used for drug delivery systems, scaffolds for tissue engineering and kits for tissue or organ regeneration.

19 Claims, 18 Drawing Sheets

Specification includes a Sequence Listing.

EBP-RBP-EBP triblock polypeptides

SELF-ASSEMBLED NANOSTRUCTURES OF ELASTIN- AND RESILIN-BASED BLOCK COPOLYPEPTIDES WITH STIMULI RESPONSIVENESS AND RESILIENCE FOR DRUG DELIVERY SYSTEM, TISSUE ENGINEERING AND REGENERATIVE MEDICINE AND METHODS OF PREPARING THE SAME

CROSS-REFERENCE TO RELATED APPLICATIONS

This application is a U.S. National Stage application of International Application No. PCT/KR2017/003113 filed on Mar. 23, 2017 and published as WO 2017/164661 A1 on Sep. 28, 2017, which claims the benefit under 35 USC 119(a) of Korean Patent Application No. 10-2016-0034372 filed Mar. 23, 2016, in the Korean Intellectual Property Office, the entire disclosures of which are incorporated herein by reference for all purposes.

BACKGROUND

1. Field of the Invention

The present disclosure relates to a self-assembled nanostructure of an elastin- and resilin-based block copolypeptide with stimuli responsiveness and resilience for drug delivery, tissue engineering and regenerative medicine, a method for preparing the same and application thereof.

2. Description of Related Art

Self-assembly of protein-based block copolymers with responsiveness to change in environments such as temperature, pH and ionic strength to micelle or hydrogel structures have been studied for decades due to high biocompatibility and controllable degradability. Protein-based block polypeptides self-assembled to core-shell micelles have gained significant attention as a drug delivery system. In particular, triblock polypeptides have been studied for tissue engineering applications because sol-gel transition occurs through physical or chemical crosslinking. Besides, various protein-based materials have been developed for drug delivery and tissue engineering applications.

Elastin-based polypeptides (EBPs) having pentapeptide repeating units, Val-Pro-(Gly or Ala)-$X_{aa}$-Gly (where $X_{aa}$ can be any amino acid except Pro) (SEQ ID NO:46 or SEQ ID NO:47), have been studied a lot due to controllable responsiveness to change in environments. The EBPs undergo reversible phase transition at the lower critical solution temperature (LCST), which is also called the transition temperature ($T_t$). They are highly water-soluble below $T_t$, but become water-insoluble as the temperature increases above the $T_t$. Generally, the physicochemical properties of EBPs are largely controlled with the combination of the pentapeptide repeating unit, Val-Pro-(Gly or Ala)-$X_{aa}$-Gly (SEQ ID NO:46 or SEQ ID NO:47). In detail, the third amino acid in the repeating unit determines the relative mechanical properties, for example, Gly for elasticity or Ala for plasticity, while the fourth amino acid, $X_{aa}$, and the multimerization of the pentapeptide repeating unit affecting the $T_t$. Depending on the unique combination of the pentapeptide repeating units, various EBPs with original physicochemical properties and $T_t$ as well as their block polypeptides can be prepared for stimuli-triggered micelle formation and hydrogelation. EBP block copolymers have been extensively studied as self-assembled micelles and injectable hydrogels for drug delivery, tissue engineering and regenerative medicine applications. The previously designed EBP diblock copolymers composed of hydrophobic blocks with lower LCST and hydrophilic blocks having higher LCST were self-assembled into micelles above the $T_t$ of the hydrophobic blocks. The self-assembly of these micelles were tuned by changing the guest residues or the molecular weights of the hydrophobic or hydrophilic blocks and inserting different chemical or functional domains.

Resilin is an elastomeric protein present in the cuticles of insects and serves a variety of functions where energy storage and repetitive movements are required. It is known for its remarkable mechanical properties, including high resilience and long fatigue lifetime. Elvin et al. cloned and expressed the first exon of the *Drosophila* CG15920 gene in *E. coli* and the resulting resilin-based polypeptide (RBP) with the putative gene sequence of GGRPSDSYGAPGGGN (SEQ ID NO:48) was called rec1-resilin. The Kristi group developed elastomeric biomaterials based on resilin-like polypeptides (RBPs) where they changed the amino acid sequence of the putative resilin repeating unit without compromising the intrinsic properties of resilin and incorporated the biologically active domains such as cell-binding RGD sequence, matrix metalloproteinase (MMP)-sensitive degradation sequence and heparin-binding domain to use them for tissue engineering applications.

They also synthesized hybrid hydrogels consisting of RLP-PEG via Michael-type reaction with a PEG-vinylsulfone crosslinker which successfully encapsulated human aortic adventitial fibroblasts in the 3D matrices with useful mechanical properties. In addition, chimeric proteins composed of sequences derived from resilin, elastin and collagen (REC) were produced which self-assembled into fibers able to support human MSC. Recently, Li et al. reported the phase separation of RBP on increasing temperature with irreversible nanoparticle formation while these RBPs didn't show any UCST behavior.

SUMMARY OF THE INVENTION

The present disclosure is directed to providing a resilin-based polypeptide exhibiting a phase transition behavior.

The present disclosure is also directed to providing a novel diblock polypeptide containing: a resilin-based polypeptide block; and a polypeptide block exhibiting a phase transition behavior, which is connected to one end of the resilin-based polypeptide block.

The present disclosure is also directed to providing a dynamic nanocarrier prepared using the diblock polypeptide.

The present disclosure is also directed to providing a novel triblock polypeptide containing: a resilin-based polypeptide block; and polypeptide blocks exhibiting a phase transition behavior, which are connected to both ends of the resilin-based polypeptide block.

The present disclosure is also directed to providing a hydrogel prepared using the triblock polypeptide.

The present disclosure is also directed to providing a drug delivery composition containing the hydrogel.

The present disclosure is also directed to providing a scaffold for tissue engineering containing the hydrogel.

The present disclosure is also directed to providing a kit for tissue or organ regeneration containing the hydrogel.

The present disclosure discloses stimuli-responsive self-assembly of a resilin-based polypeptide (RBP) and an elastin-based polypeptide (EBP) for micelle and hydrogel formation. A series of EBPP-RBP diblock and EBPP-RBP-EBPP triblock peptides were synthesized by genetic engineering techniques and purified by ITC (inverse transition cycling). The EBPP-RBP diblock polypeptides were self-assembled into micelle structures depending on the hydrophobic and hydrophilic nature of the blocks and the micelle structures showed dynamic change depending on the lower critical solution temperature (LOST) of EBPP and the upper critical solution temperature (UCST) of RBP. And, the EBPP-RBP-EBPP triblock polypeptides showed physical crosslinking of EBP above the lower critical solution temperature (LOST) of EBPP, resulting in hydrogel networks and reversible sol-gel transition. Furthermore, the mechanical strength of the resulting hydrogels could be enhanced through chemical crosslinking between the RBP blocks and enhanced hydrophobicity of the EBP blocks. Accordingly, the self-assembly of the elastin- and resilin-based polypeptides into micelles and the dynamic hydrogels with improved mechanical properties would have great potential for biomedical applications.

The present disclosure provides a resilin-based polypeptide (RBP) exhibiting a phase transition behavior, which contains an amino acid sequence represented by SEQ ID NO:44.

In the present disclosure, resilin is an elastomeric protein present in the cuticles of insects and serves a variety of functions where energy storage and repetitive movements are required. It is known for its remarkable mechanical properties, including high resilience and long fatigue lifetime. Elvin et al. cloned and expressed the first exon of the *Drosophila* CG15920 gene in *E. coli* and discovered the putative sequence of the resilin polypeptide. In the present disclosure, a resilin-based polypeptide exhibiting a phase transition behavior while maintaining superior mechanical properties was prepared by partly changing the sequence. Specifically, the gene sequence of the resilin-based polypeptide may be SEQ ID NO:42, although not being limited thereto.

The present disclosure provides a diblock polypeptide with stimuli responsiveness, represented by Formula 1, which contains:
 a resilin-based polypeptide block; and
 a polypeptide block exhibiting a phase transition behavior, which is connected to one end of the resilin-based polypeptide block:
[Formula 1]
[hydrophobic EBP]$_m$-[RBP]$_n$
wherein
n or m is independently an integer 1 or greater,
the [RBP] is a resilin-based polypeptide block containing an amino acid sequence represented by SEQ ID NO:44, and
the [hydrophobic EBP] is a [VPGXG VPGXG VPGXG VPGXG VPGXG VPGXG] block of SEQ ID NO:1, a [VPAXG VPAXG VPAXG VPAXG VPAXG VPAXG] block of SEQ ID NO:2, or an [IPAXG IPAXG IPAXG IPAXG IPAXG IPAXG] block of SEQ ID NO:3 (wherein X is any natural or artificial amino acid except proline, and wherein the pentapeptide of VPGXG (SEQ ID NO:46), VPAXG (SEQ ID NO:47), or IPAXG (SEQ ID NO:49) is repeated).

The term "amino acid" used in the present disclosure refers to a natural amino acid or an artificial amino acid, specifically a natural amino acid. For example, the amino acid refers to glycine, alanine, serine, valine, leucine, isoleucine, methionine, glutamine, asparagine, cysteine, histidine, phenylalanine, arginine, tyrosine, tryptophan, etc.

The properties of these amino acids are well known in the art. Specifically, they exhibit hydrophilic (negatively or positively charged) or hydrophobic properties and also exhibit aliphatic or aromatic properties.

The abbreviations such as Gly (G), Ala (A), etc. used in the present disclosure are the abbreviations of amino acids. Gly stands for glycine and Ala for alanine. Glycine is also represented by G and alanine by A. These abbreviations are widely used in the art.

In the present disclosure, a "hydrophobic amino acid" refers to an amino acid exhibiting hydrophobic properties, such as phenylalanine, leucine, etc.

The term "polypeptide" used in the present disclosure refers to any polymer chain of amino acids. The terms "peptide" and "protein", which may be used interchangeably with the polypeptide, also refer to a polymer chain of amino acids. The term "polypeptide" includes a natural or synthetic protein, a protein fragment and a polypeptide analog of a protein sequence. The polypeptide may be either a monomer or a polymer.

The term "phase transition" refers to change in the state of a material, for example, from water to water vapor or from ice to water.

The polypeptide exhibiting a phase transition behavior according to the present disclosure is basically a stimuli-responsive elastin-based polypeptide (EBP). The "elastin-based polypeptide" is also called an "elastin-like polypeptide (ELP)". These terms are widely used in the art to which the present disclosure belongs.

In the present disclosure, the X (or X$_{aa}$) is called a "guest residue". EBPs of various kinds according to the present disclosure can be prepared by introducing different X$_{aa}$'s.

The EBP undergoes reversible phase transition at the lower critical solution temperature (LOST), which is also called the transition temperature (T$_t$). It is highly water-soluble below T$_t$, but becomes insoluble as the temperature increases above the T$_t$.

In the present disclosure, the physicochemical properties of the EBP are largely controlled with the combination of a pentapeptide repeating unit, e.g., Val-Pro-(Gly or Ala)-X$_{aa}$-Gly [VP(G or A)XG] (SEQ ID NO:46 or SEQ ID NO:47). In detail, the third amino acid in the repeating unit determines relative mechanical properties. For example, as the third amino acid, Gly determines elasticity or Ala determines plasticity. The elasticity or plasticity is exhibited after phase transition. Meanwhile, both the hydrophobicity of the guest residue X$_{aa}$, which is the fourth amino acid, and the multimerization of the pentapeptide repeating unit affect the T$_t$.

The EBP according to the present disclosure may be a polypeptide wherein pentapeptides are repeated and the repeating polypeptides may form a polypeptide block (EBP block). Specifically, they may form a hydrophilic EBP block or a hydrophobic EBP block.

The hydrophilic or hydrophilic nature of the EBP block of the present disclosure is closely related with the transition temperature of the EBP. And, the transition temperature of the EBP also depends on the amino acid sequence and molecular weight. In the Val-Pro-Gly-Val-Gly (SEQ ID NO:50) pentapeptide, if the fourth amino acid, or the "guest residue", is substituted with a residue exhibiting higher hydrophilicity than Val, the T$_t$ is increased as compared to the original sequence. Conversely, if the guest residue is substituted with a residue which is more hydrophobic than Val, the T$_t$ is decreased as compared to the original sequence. That is to say that, it was discovered that a hydrophilic EBP exhibits a relatively higher T$_t$ and a hydrophobic EBP exhibits a lower $T_t$. Based on this finding, an EBP having a specific $T_t$ can be prepared by determining which amino acid will be used as the guest residue of the EBP sequence and changing the composition of the guest residue.

As described above, a higher $T_t$ leads to hydrophilicity and a lower $T_t$ leads to hydrophobicity. The $T_t$ of the EBP blocks according to the present disclosure can also be raised or lowered by changing the amino acid sequence and molecular weight. Through this, it is possible to prepare a hydrophobic EBP block.

For reference, an EBP having a $T_t$ lower than the body temperature may be used as a hydrophobic block. Due to this nature of the EBP, the hydrophilic and hydrophobic properties of the EBP may be defined relatively for bioengineering applications.

For example, when comparing a polypeptide block with plasticity wherein the plastic pentapeptide Val-Pro-Ala-$X_{aa}$-Gly (SEQ ID NO:47) is repeated and a pentapeptide with elasticity wherein the elastic pentapeptide Val-Pro-Gly-$X_{aa}$-Gly (SEQ ID NO:46) is repeated, a higher hydrophilicity is exhibited when the third amino acid is Gly than when it is Ala. Accordingly, the elastin-based polypeptide with plasticity (EBPP) shows a lower $T_t$ than the elastin-based polypeptide with elasticity (EBPE).

In a specific exemplary embodiment, the [hydrophobic EBP] may be a [VPGXG VPGXG VPGXG VPGXG VPGXG VPGXG] block of SEQ ID NO:1, wherein each X of the repeating pentapeptide contains:

[SEQ ID NO: 23]
A (Ala), G (Gly) and I (Ile) at a ratio of 1:4:1;

[SEQ ID NO: 25]
K (Lys), G (Gly) and I (Ile) at a ratio of 1:4:1;

[SEQ ID NO: 27]
D (Asp), G (Gly) and I (Ile) at a ratio of 1:4:1;

[SEQ ID NO: 29]
E (Glu), G (Gly) and I (Ile) at a ratio of 1:4:1;
or

[SEQ ID NO: 31]
G (Gly), A (Ala) and F (Phe) at a ratio of 1:3:2.

Specifically, the gene sequence of the polypeptide may be SEQ ID NO:4 (sequence corresponding to SEQ ID NO:23), SEQ ID NO:6 (sequence corresponding to SEQ ID NO:25), SEQ ID NO:8 (sequence corresponding to SEQ ID NO:27), SEQ ID NO:10 (sequence corresponding to SEQ ID NO:29) or SEQ ID NO:12 (sequence corresponding to SEQ ID NO:31).

In another specific exemplary embodiment, the [hydrophobic EBP] may be a [VPAXG VPAXG VPAXG VPAXG VPAXG VPAXG] block of SEQ ID NO:2, wherein each X of the repeating pentapeptide contains:

[SEQ ID NO: 32]
G (Gly), A (Ala) and F (Phe) at a ratio of 1:3:2;

[SEQ ID NO: 33]
K (Lys), A (Ala) and F (Phe) at a ratio of 1:3:2;

[SEQ ID NO: 34]
D (Asp), A (Ala) and F (Phe) at a ratio of 1:3:2;

[SEQ ID NO: 35]
K (Lys) and F (Phe) at a ratio of 3:3;

[SEQ ID NO: 36]
D (Asp) and F (Phe) at a ratio of 3:3;

[SEQ ID NO: 37]
H (His), A (Ala) and I (Ile) at a ratio of 3:2:1;

[SEQ ID NO: 38]
H (His) and G (Gly) at a ratio of 5:1;
or

[SEQ ID NO: 39]
G (Gly), C (Cys) and F (Phe) at a ratio of 1:3:2.

Specifically, the gene sequence of the polypeptide may be SEQ ID NO:13 (corresponding to SEQ ID NO:32), SEQ ID NO:14 (corresponding to SEQ ID NO:33), SEQ ID NO:15 (corresponding to SEQ ID NO:34), SEQ ID NO:16 (corresponding to SEQ ID NO:35), SEQ ID NO:17 (corresponding to SEQ ID NO:36), SEQ ID NO:18 (corresponding to SEQ ID NO:37), SEQ ID NO:19 (corresponding to SEQ ID NO:38) or SEQ ID NO:20 (corresponding to SEQ ID NO:39).

In another specific exemplary embodiment, the [hydrophobic EBP] may be an [IPAXG IPAXG IPAXG IPAXG IPAXG IPAXG] block of SEQ ID NO:3, wherein each X of the repeating pentapeptide contains:

[SEQ ID NO: 40]
G (Gly), A (Ala) and F (Phe) at a ratio of 1:4:1;
or

[SEQ ID NO: 41]
G (Gly), A (Ala) and F (Phe) at a ratio of 1:3:2.

Specifically, the gene sequence of the polypeptide may be SEQ ID NO:21 (corresponding to SEQ ID NO:40) or SEQ ID NO:22 (corresponding to SEQ ID NO:41).

The dynamic change of the diblock polypeptide of [Formula 1] according to the present disclosure is schematically shown in FIG. 5B.

The resilin-based polypeptide block (RBP) and the elastin-based polypeptide block (EBP) exhibiting a phase transition behavior, which constitute the diblock polypeptide, are blocks having hydrophilic and hydrophobic properties, respectively, and greatly contribute to formation of a micelle structure. First, below the LOST of the EBP, a self-assembled micelle structure consisting of a core formed of the RBP block in aggregated state and a shell formed of the EBP block in solubilized state is formed. Above the LOST of the EBP, the EBP block is also aggregated and an aggregate is formed as a whole. Finally, at high temperatures above the UCST of the RBP, the RBP is solubilized and a micelle structure consisting of a core formed of the EBP block in aggregated state and a shell formed of the RBP block in solubilized state is formed again. In particular, the UCST of the RBP can be controlled by varying the length or molecular weight of the diblock polypeptide and this change of the micelle structure is reversible.

The term "self-assembly" used in the present disclosure refers to formation of a specific structure through spontaneous assembly. In the context of the present disclosure, the self-assembly means the formation of a micelle nanostructure depending on the difference in degree of solubilization at specific temperature as a hydrophobic domain or a core is formed and a hydrophilic domain or a shell is formed.

That is to say, the RBP-EBP diblock polypeptide-based micelle nanostructure exhibits a reversible dynamic behavior in response to temperature and this property can be controlled with the length of the diblock polypeptide or each block. Accordingly, the stimuli-responsive RBP-EBP diblock polypeptide exhibiting stimuli-induced drug release kinetics will be useful for dynamic drug delivery systems.

The present disclosure provides a triblock polypeptide with stimuli responsiveness, represented by Formula 2, which contains:
a resilin-based polypeptide block; and
polypeptide blocks exhibiting a phase transition behavior, which are connected to both ends of the resilin-based polypeptide block:
[Formula 2]
[hydrophobic EBP]$_m$-[RBP]$_n$-[hydrophobic EBP]$_m$
wherein
n or m is independently an integer 1 or greater,
the [RBP] is a resilin-based polypeptide block containing an amino acid sequence represented by SEQ ID NO:44, and
the [hydrophobic EBP] is a [VPGXG VPGXG VPGXG VPGXG VPGXG VPGXG] block of SEQ ID NO:1, a [VPAXG VPAXG VPAXG VPAXG VPAXG VPAXG] block of SEQ ID NO:2, or an [IPAXG IPAXG IPAXG IPAXG IPAXG IPAXG] block of SEQ ID NO:3 (wherein X is any natural or artificial amino acid except proline, and wherein the pentapeptide of VPGXG (SEQ ID NO:46), VPAXG (SEQ ID NO:47), or IPAXG (SEQ ID NO:49) is repeated).

The triblock polypeptide of the present disclosure uses the resilin-based polypeptide block and the polypeptide block exhibiting a phase transition behavior described above with respect to the diblock polypeptide. Therefore, description thereof will be omitted to avoid unnecessary repetition.

In another aspect, the present disclosure provides a hydrogel prepared by a process including:
a step of applying temperature stimuli to the triblock polypeptide of the present disclosure; and
a step of forming crosslinkages between the triblock polypeptide in response to the temperature stimuli.

In the present disclosure, the term "hydrogel" generally refers to a material having a 3-dimensional hydrophilic polymer network structure capable of holding a large quantity of water. In aqueous solutions, it is swollen and remains thermodynamically stably, exhibiting mechanical and physicochemical properties between those of liquid and solid.

The dynamic change of the triblock polypeptide of [Formula 2] according to the present disclosure is schematically shown in FIG. 5C.

First, below the lower critical solution temperature of EBPP, an EBPP-RBP-EBPP triblock polypeptide exists in a solubilized state. Above the lower critical solution temperature of the EBPP, a dynamic hydrogel is formed as reversible gelation occurs through physical crosslinking. During this process, the RBP block serves as an elastic block and also serves to enhance the mechanical properties of the entire hydrogel by as chemical crosslinkages are formed between the tyrosine residues of the middle block.

The [IPAXG IPAXG IPAXG IPAXG IPAXG IPAXG] block of SEQ ID NO:3, wherein the first amino acid "Val" of the repeating pentapeptide in the [hydrophobic EBP] block is substituted with "Ile" exhibits enhanced hydrophobic property. Therefore, a hydrogel using the block shows improved mechanical properties.

The "dynamic hydrogel" refers to a material (e.g., a protein) which forms a hydrogel by undergoing 3-dimensional conformational change in response to environmental changes (temperature, pH, ionic strength, ligand, etc.).

In another aspect, the present disclosure provides a drug delivery composition containing the hydrogel. Because the hydrogel responds to temperature stimuli, it can stably deliver a drug into the body.

In another aspect, the present disclosure provides a scaffold for tissue engineering containing the hydrogel. The scaffold for tissue engineering according to the present disclosure includes any scaffold that can be used in the field of tissue engineering for the purpose of maintaining, improving or restoring the body function by preparing and implanting biological substitutes.

In another aspect, the present disclosure provides a kit for tissue or organ regeneration containing the hydrogel. The kit for tissue or organ regeneration according to the present disclosure may contain, in addition to the scaffold for tissue engineering, a reinforcing layer for maintaining the shape of the scaffold. The reinforcing layer may be selected from a biodegradable polymer material such as PCL, PLA, PLGA, PGA, etc.

The present disclosure relates to a diblock/triblock polypeptide with stimuli responsiveness, consisting of a resilin-based polypeptide and a polypeptide exhibiting a phase transition behavior, and a use thereof. The diblock polypeptide reversibly forms a self-assembled micelle structure in response to temperature stimuli and a hydrogel prepared using the triblock polypeptide undergoes reversible sol-gel or gel-sol transition in response to temperature stimuli and exhibits enhanced mechanical strength due to chemical crosslinkages between tyrosine residues. With such superior properties, the diblock/triblock polypeptide of the present disclosure can be used for drug delivery systems, scaffolds for tissue engineering and kits for tissue or organ regeneration.

BRIEF DESCRIPTION OF THE DRAWINGS

FIG. 1A illustrates an example for RDL, an adapter sequence containing AcuI and BseRI restriction enzyme sites was inserted into pET-21(a). The RBP nucleotide cassette (with AcuI and BseRI sticky ends) was inserted into the BseRI-restricted modified pET-21(a). FIG. 1B illustrates an example of the RBP gene multimerized by RDL. The vector was linearized by XbaI and BseRI and an insert was restricted by XbaI and AcuI. After ligation, the same procedure was repeated until the desired gene length was achieved. FIG. 1C illustrates an example of a diblock polypeptide cloned by inserting the EBPP gene into a RBP-containing plasmid (linearized by XbaI and BseRI). FIG. 1D illustrates an example of a seamless triblock polypeptide. In the first step, a diblock was synthesized by inserting the EBPP gene into a RBP plasmid. In the second step, a triblock polypeptide, EBPP-RBP-EBPP, synthesized by inserting the EBPP gene (restricted by XbaI and AcuI) into the plasmid containing the diblock.

FIG. 3A illustrates an example of the result of thermal profiling of RBP[m-Dros]$_{24}$. FIG. 3B illustrates an example of the result of thermal profiling of RBP[m-Dros]$_{30}$. FIG. 3C illustrates an example of the result of thermal profiling of RBP[Dros]$_8$. The lane (M) shows size markers in kDa unit and the expected molecular weights are labeled on the right side. FIG. 3D describes an example of the thermal profile of RBP[Dros]$_{16}$ at 25, 50, and 100 µM in PBS. The thermal profile data were collected by heating the protein solution from 10° C. to 90° C. at a heating rate of 1° C./min.

FIG. 5A illustrates an example of the RBP[m-Dros]$_n$ monoblock with tyrosine residues shows reversible thermal transition. The RBP is completely soluble above the UCST and is aggregated when cooled below the UCST. FIG. 5B illustrates an example of the EBPP-RBP[m-Dros]$_n$ diblock polypeptide with hydrophilic RBP and hydrophobic EBPP self-assemble into a micelle structure. Below the T$_t$ of EBPP, the RBP is aggregated to form a core of the micelle whereas the EBP in solubilized state forms a shell. Above the T$_t$ of EBPP, the EBPP is aggregated as a whole through thermal transition. At very high temperatures of –80° C., the RBP becomes soluble and a micelle is formed again. This thermal responsiveness of the diblock peptide is reversible. FIG. 5C illustrates an example of the EBPP-RBP-EBPP triblock polypeptide has a middle RBP block containing tyrosine residues which is flanked by hydrophobic EBPP blocks. Below the T$_t$ of EBPP, the EBP-RBP-EBPP triblock polypeptide is in solubilized state. Above the T$_t$ of EBPP, a physically crosslinked protein hydrogel is formed through thermally triggered reversible gelation. Chemical crosslinkages formed between the tyrosine residues on the middle block may enhance the mechanical properties of the hydrogel.

FIG. 7B shows a result of measuring the size of EBPP[G$_1$A$_3$F$_2$]$_6$-RBP[m-Dros]$_{24}$ at 25° C. and 85° C. by DLS.

FIG. 8A illustrates an example of diblock polypeptide and FIG. 8B illustrates an example of triblock polypeptide having EBPP[G$_1$A$_3$F$_2$]$_{12}$. The thermal transition pattern was the same in the two plots. The polypeptides were in solubilized state at low temperature and were aggregated as the temperature was increased.

FIG. 10A, 37° C. FIG. 10B and FIGS. 10C and 4° C. FIG. 10D. Its gel-sol transition behavior was reversible as the temperature was decreased from 37° C. to 4° C. which indicated the reversibility of physically crosslinked gel.

FIG. 12A illustrates an example of the amplitude sweep (0.2-20% at a frequency of 1 rad/s). FIG. 12B illustrates an example of the frequency sweep (0.1-10 rad/s at 2% strain). FIG. 12C and FIG. 12D show the rheological behavior as a function of temperature at a heating and cooling rate of 1° C./min (strain 2%, 1 rad/s).

DETAILED DESCRIPTION OF THE INVENTION

Figure 1A:
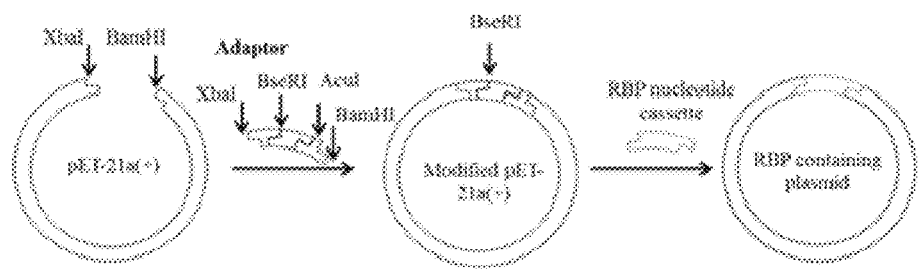
FIGS. 1A-1D schematically describes cloning of RBP, monoblock, diblock and triblock polypeptide genes.

Hereinafter, specific examples are presented to help understanding the present disclosure. However, the following examples are given only to help better understanding of the present disclosure and the present disclosure is not limited by the examples.

EXAMPLES

Example 1. Materials

The pET-21a vector and BL21 (DE3) *E. coli* cells were obtained from Novagen Inc. (Madison, Wisconsin, US). Top10 competent cells were obtained from Invitrogen (Carlsbad, California, US). Oligonucleotides were synthesized chemically at Cosmo Gene Tech (Seoul, South Korea). The FastAP thermosensitive alkaline phosphatase and restriction endonuclease including BamHI and XbaI were purchased from Fermentas (Ontario, Canada). Other restriction endonuclease including BseRI and AcuI and all other restriction enzymes were obtained from New England Biolabs (Ipswich, Massachusetts, US). DNA miniprep, gel extraction and PCR purification kits were obtained from Geneall Biotechnology (Seoul, South Korea). Dyne Agarose High was obtained from Dyne Bio, Inc. (Seongnam, South Korea). All the Top10 cells were grown in TB DRY media obtained from MO Bio Laboratories, Inc. (Carlsbad. California, US). All the BL21 (DE3) cells were grown in CircleGrow media obtained from MP Biomedicals (Solon, Ohio, US). Ready Gel (Tris-HCl 2-20%) as a precast gel was purchased from Bio-Rad (Hercules, California, US). Phosphate-buffered saline (PBS, pH 7.4), ampicillin and polyethyleneimine (PEI) were obtained from Sigma-Aldrich (St Louis, Missouri).

Example 2. Notation for Different EBP Blocks and their Block Polypeptides

Different EBPs with a pentapeptide repeating unit, Val-Pro-(Gly or Ala)-$X_{aa}$-Gly [VP(G or A)XG], where $X_{aa}$ can be any amino acid except Pro (SEQ ID NO:46 or SEQ ID NO:47), are named as follows. First, the pentapeptide repeat of Val-Pro-Ala-$X_{aa}$-Gly (VPAXG) (SEQ ID NO:47) with plasticity is defined as an elastin-based polypeptide with plasticity (EBPP) while the pentapeptide repeat of Val-Pro-Gly-$X_{aa}$-Gly (VPGXG) (SEQ ID NO:46) being called an elastin-based polypeptide with elasticity (EBPE). And, the pentapeptide repeat of Ile-Pro-Ala-$X_{aa}$-Gly (IPAXG) (SEQ ID NO:49) wherein the first amino acid is substituted with Ile is defined as an elastin-based polypeptide with plasticity and substituted with Ile (EBPPI). Secondly, $[X_iY_jZ_k]_n$ represents that the bracketed capital letters are single letter amino acid codes of the guest residues, i.e. the amino acid at the fourth position ($X_{aa}$ or X) in the EBP pentapeptide, and their corresponding subscripts denote the ratio of that guest residue in the EBP monomer gene as the repeating unit. The subscript number n of $[X_iY_jZ_k]_n$ indicates the total repeating number of SEQ ID NO:1 [VPGXG VPGXG VPGXG VPGXG VPGXG VPGXG],-SEQ ID NO:2 [VPAXG VPAXG VPAXG VPAXG VPAXG VPAXG], or SEQ ID NO:3 [IPAXG IPAXG IPAXG IPAXG IPAXG IPAXG] in the EBP. For example, EBPP[$G_1A_3F_2$]$_{12}$ is an EBPP block that contains 12 repeats of SEQ ID NO:2 [VPAXG VPAXG VPAXG VPAXG VPAXG VPAXG], in which the ratio of Gly, Ala and Phe at the fourth guest residue position ($X_{aa}$) is 1:3:2.

Two RBPs having different sequences are named as RBP[Dros]$_n$ and RBP[m-Dros]$_n$, where n represents the number of repeating unit. Both sequences are derived from *Drosophila* exon 1 and the RBP repeating unit contains two repeating sequences of resilin. For RBP[Dros]$_n$, the repeating sequences are the same as reported in previous studies while, for RBP[m-Dros]$_n$, the two repeating sequences of resilin are combined with slight modifications to get the desired properties such as temperature responsiveness and high resilience. The EBPP-RBP diblock and triblock polypeptides are named by the composition of each block in square brackets with a hyphen between blocks such as EBPP[$G_1A_3F_2$]$_n$-RBP[Dros/m-Dros]$_n$ for a diblock and EBPP[$G_1A_3F_2$]$_n$-RBP[Dros/m-Dros]$_n$-EBPP[$G_1A_3F_2$]$_n$ for a triblock.

Example 3. Preparation of Modified pET-21a Vector for Seamless Gene Cloning

As shown in FIG. 1A, pET-21a(+) was modified to introduce two unique restriction sites BseRI and AcuI for RDL of EBP and RBP. 4 µg of the pET-21a(+) vector was digested with 50 U of XbaI and 50 U of BamHI in FastDigest buffer for 20 minutes at 37° C. The 5' end was dephosphorylated with 10 U of CIP in NEB 3 buffer for 1 hour at 37° C. The restricted plasmid DNA was purified using the PCR purification kit and was eluted in 40 µL of distilled deionized water. Two oligonucleotide sequences with XbaI and BamHI sticky ends having BseRI and AcuI restriction sites having XbaI- and BamHI-compatible sticky ends were designed: 5'-ctagaaataattttgtttaactttaagaa ggaggagtacatatgggcta ctgataatgatcttcag-3' (SEQ ID NO:51) and 5'-gatcctgaagatcattatcagtagcccatatgtactcctcc ttcttaaagttaaacaaaattattt-3' (SEQ ID N0:52). This oligonucleotide DNA also contains Tyr for spectrophotometric detection of proteins and start (Met) and stop codons. 50 µl of the two oligonucleotides were annealed at 2 µM concentration of each nucleotide in T4 DNA ligase buffer at 95° C. for 2 minutes and then slowly cooled down to the room temperature over 3 hours. The modified cloning insert with XbaI and BamHI stick ends was inserted into the linearized pET-21a(+) vector by incubating with 20 pmol of annealed dsDNA and 0.1 pmol of the linearized vector in T4 DNA ligase buffer containing T4 DNA ligase at 16° C. for 30 minutes. The ligated vector was introduced into chemically transformed Top 10 competent cells, followed by plating on SOC (Super Optimal Broth with catabolite repression) plates supplemented with 50 µg/mL of ampicillin. The insert sequence was confirmed by DNA sequencing.

Example 4. Monomer Gene Synthesis and Oligomerization for RBP and EBP

The EBP sequences with a pentapeptide repeating unit, Val-Pro-(Gly or Ala)-$X_{aa}$-Gly (SEQ ID NO:46 or SEQ ID NO:47), where the fourth residues are varied at different molar ratios were designed at DNA level to optimize $T_t$ below the physiological temperature. The DNA and amino acid sequences of the EBPs with various pentapeptide repeating units are shown in Table 1 and Table 2, respectively.

TABLE 1

Gene sequences of EBP libraries

| EBP | Gene Sequence |
|---|---|
| EBPE[$A_1G_4I_1$] (SEQ ID NO: 4) | GTC CCA GGT GGA GGT GTA CCC GGC GCG GGT GTC CCA GGT GGA GGT GTA CCT GGG GGT GGG GTC CCT GGT ATT GGC GTA CCT GGA GGC GGC |
| EBPP[$A_1G_4I_1$] (SEQ ID NO: 5) | GTT CCA GCT GGC GGT GTA CCT GCT GCT GCT GTT CCG GCC GGT GGT GTT CCG GCG GGC GGC GTG CCT GCA ATA GGA GTT CCC GCT GGT GGC |
| EBPE[$K_1G_4I_1$] (SEQ ID NO: 6) | GTT CCG GGT GGT GGT GTT CCG GGT AAA GGT GTT CCG GGT GGT GGT GTT CCG GGT GGT GGT GTT CCG GGT ATC GGT GTT CCG GGT GGC |
| EBPP[$K_1G_4I_1$] (SEQ ID NO: 7) | GTT CCG GCG GGT GGT GTT CCG GCG AAA GGT GTT CCG GCG GGT GGT GTT CCG GCG GGT GGT GTT CCG GCG ATC GGT GTT CCG GCG GGT GGC |

TABLE 1-continued

Gene sequences of EBP libraries

| EBP | Gene Sequence |
|---|---|
| EBPE[$D_1G_4I_1$]<br>(SEQ ID NO: 8) | GTT CCG GGT GGT GGT GTT CCG GGT GAT GGT GTT CCG GGT GGT GGT<br>GTT CCG GGT GGT GGT GGT GTT CCG GGT ATC GGT GTT CCG GGT GGC |
| EBPP[$D_1G_4I_1$]<br>(SEQ ID NO: 9) | GTT CCG GCG GGT GGT GTT CCG GCG GAT GGT GTT CCG GCG GGT GGT<br>GTT CCG GCG GGT GGT GTT CCG GCG ATC GGT GTT CCG GCG GGT GGC |
| EBPE[$E_1G_4I_1$]<br>(SEQ ID NO: 10) | GTT CCG GGT GGT GGT GTT CCG GGT GAA GGT GTT CCG GGT GGT GGT<br>GTT CCG GGT GGT GGT GGT GTT CCG GGT ATC GGT GTT CCG GGT GGC |
| EBPP[$E_1G_4I_1$]<br>(SEQ ID NO: 11) | GTT CCG GCG GGT GGT GTT CCG GCG GAA GGT GTT CCG GCG GGT GGT<br>GTT CCG GCG GGT GGT GTT CCG GCG ATC GGT GTT CCG GCG GGT GGC |
| EBPE[$G_1A_3F_2$]<br>(SEQ ID NO: 12) | GTC CCG GGT GCG GGC GTG CCG GGA TTT GGA GTT CCG GGT GCG GGT<br>GTT CCA GGC GGT GGT GTT CCG GGC GCG GGC GTG CCG GGC TTT GGC |
| EBPP[$G_1A_3F_2$]<br>(SEQ ID NO: 13) | GTG CCG GCG GCG GGC GTT CCA GCC TTT GGT GTG CCA GCG GCG GGA<br>GTT CCG GCC GGT GGC GTG CCG GCA GCG GGC GTG CCG GCT TTT GGC |
| EBPP[$K_1A_3F_2$]<br>(SEQ ID NO: 14) | GTG CCG GCG GCG GGC GTT CCA GCC TTT GGT GTG CCA GCG GCG GGA<br>GTT CCG GCC AAA GGC GTG CCG GCA GCG GGC GTG CCG GCT TTT GGC |
| EBPP[$D_1A_3F_2$]<br>(SEQ ID NO: 15) | GTG CCG GCG GCG GGC GTT CCA GCC TTT GGT GTG CCA GCG GCG GGA<br>GTT CCG GCC GAT GGC GTG CCG GCA GCG GGC GTG CCG GCT TTT GGC |
| EBPP[$K_3F_3$]<br>(SEQ ID NO: 16) | GTT CCA GCG TTT GGC GTG CCA GCG AAA GGT GTT CCG GCG TTT GGG<br>GTT CCC GCG AAA GGT GTG CCG GCC TTT GGT GTG CCG GCC AAA GGC |
| EBPP[$D_3F_3$]<br>(SEQ ID NO: 17) | GTT CCA GCG TTT GGC GTG CCA GCG GAT GGT GTT CCG GCG TTT GGG<br>GTT CCC GCG GAT GGT GTG CCG GCC TTT GGT GTG CCG GCC GAT GGC |
| EBPP[$H_3A_3I_1$]<br>(SEQ ID NO: 18) | GTG CCG GCG CAT GGA GTT CCT GCC GCC GGT GTT CCT GCG CAT GGT<br>GTA CCG GCA ATT GGC GTT CCG GCA CAT GGT GTG CCG GCC GCC GGC |
| EBPP[$H_5G_1$]<br>(SEQ ID NO: 19) | GTT CCG GCC GGA GGT GTA CCG GCG CAT GGT GTT CCG GCA CAT GGT<br>GTG CCG GCT CAC GGT GTG CCT GCG CAT GGC GTT CCT GCG CAT GGC |
| EBPP[$G_1C_3F_2$]<br>(SEQ ID NO: 20) | GTG CCG GCG TGC GGC GTT CCA GCC TTT GGT GTG CCA GCG TGC GGA<br>GTT CCG GCC GGT GGC GTG CCG GCA TGC GGC GTG CCG GCT TTT GGC |
| EBPPI[$G_1A_4F_1$]<br>(SEQ ID NO: 21) | ATT CCT GCA GCC GGT ATC CCG GCC GGT GGC ATT CCG GCA GCC GGC<br>ATT CCG GCC GCC GGC ATC CCG GCA TTT GGC ATT CCT GCA GCA GGC |
| EBPPI[$G_1A_3F_2$]<br>(SEQ ID NO: 22) | ATT CCG GCC GCA GGC ATT CCT GCA TTT GGT ATT CCG GCG GCA GGC<br>ATT CCT GCC GGT GGC ATC CCG GCA GCG GGC ATT CCG GCC TTT GGC |

TABLE 2

Amino acid sequences of EBP libraries

| EBP | Amino Acid Sequence | | | | | |
|---|---|---|---|---|---|---|
| EBPE[$A_1G_4I_1$]<br>(SEQ ID NO: 23) | VPGGG | VPGAG | VPGGG | VPGGG | VPGIG | VPGGG |
| EBPP[$A_1G_4I_1$]<br>(SEQ ID NO: 24) | VPAGG | VPAAG | VPAGG | VPAGG | VPAIG | VPAGG |
| EBPE[$K_1G_4I_1$]<br>(SEQ ID NO: 25) | VPGGG | VPGKG | VPGGG | VPGGG | VPGIG | VPGGG |
| EBPP[$K_1G_4I_1$]<br>(SEQ ID NO: 26) | VPAGG | VPAKG | VPAGG | VPAGG | VPAIG | VPAGG |
| EBPE[$D_1G_4I_1$]<br>(SEQ ID NO: 27) | VPGGG | VPGDG | VPGGG | VPGGG | VPGIG | VPGGG |
| EBPP[$D_1G_4I_1$]<br>(SEQ ID NO: 28) | VPAGG | VPADG | VPAGG | VPAGG | VPAIG | VPAGG |
| EBPE[$E_1G_4I_1$]<br>(SEQ ID NO: 29) | VPGGG | VPGEG | VPGGG | VPGGG | VPGIG | VPGGG |

TABLE 2-continued

Amino acid sequences of EBP libraries

| EBP | Amino Acid Sequence | | | | | |
|---|---|---|---|---|---|---|
| EBPP[E$_1$G$_4$I$_1$] (SEQ ID NO: 30) | VPAGG | VPAEG | VPAGG | VPAGG | VPAIG | VPAGG |
| EBPE[G$_1$A$_3$F$_2$] (SEQ ID NO: 31) | VPGAG | VPGFG | VPGAG | VPGGG | VPGAG | VPGFG |
| EBPP[G$_1$A$_3$F$_2$] (SEQ ID NO: 32) | VPAAG | VPAFG | VPAAG | VPAGG | VPAAG | VPAFG |
| EBPP[K$_1$A$_3$F$_2$] (SEQ ID NO: 33) | VPAAG | VPAFG | VPAAG | VPAGG | VPAAG | VPAFG |
| EBPP[D$_1$A$_3$F$_2$] (SEQ ID NO: 34) | VPAAG | VPAFG | VPAAG | VPAGG | VPAAG | VPAFG |
| EBPP[K$_3$F$_3$] (SEQ ID NO: 35) | VPAFG | VPAKG | VPAFG | VPAKG | VPAFG | VPAKG |
| EBPP[D$_3$F$_3$] (SEQ ID NO: 36) | VPAFG | VPADG | VPAFG | VPADG | VPAFG | VPADG |
| EBPP[H$_3$A$_3$I$_1$] (SEQ ID NO: 37) | VPAHG | VPAAG | VPAHG | VPAIG | VPAHG | VPAAG |
| EBPP[H$_5$G$_1$] (SEQ ID NO: 38) | VPAGG | VPAHG | VPAHG | VPAHG | VPAHG | VPAHG |
| EBPP[G$_1$C$_3$F$_2$] (SEQ ID NO: 39) | VPACG | VPAFG | VPACG | VPAGG | VPACG | VPAFG |
| EBPPI[G$_1$A$_4$F$_1$] (SEQ ID NO: 40) | IPAAG | IPAGG | IPAAG | IPAAG | IPAFG | IPAAG |
| EBPPI[G$_1$A$_3$F$_2$] (SEQ ID NO: 41) | IPAAG | IPAFG | IPAAG | IPAGG | IPAAG | IPAFG |

In Table 1, SEQ ID NOS 4-11 may be classified as gene sequences for hydrophilic EBP blocks and SEQ ID NOS 12-22 may be classified as gene sequences for Phe- and His-containing hydrophobic EBP blocks. In Table 2, SEQ ID NOS 23-30 may be classified as hydrophilic and SEQ ID NOS 31-41 containing Phe and His may be classified as hydrophobic EBP blocks. That is to say, hydrophobicity is exhibited when the LCST of EBP is below the body temperature and hydrophilicity is exhibited when the LCST of EBP is above the body temperature. Therefore, the hydrophilicity and hydrophobicity of the EBP may be defined relatively with regard to bioengineering applications.

Different EBPs having the pentapeptide repeating unit Val-Pro-(Gly or Ala)-X$_{aa}$-Gly [where X$_{aa}$ can be any amino acid except Pro] (SEQ ID NO:46 or SEQ ID NO:47) were designed at DNA level to have unique responsiveness to stimuli including temperature and pH. Both the EBP with plasticity (EBPP) having the Val-Pro-Ala-X$_{aa}$-Gly (VPAXG) (SEQ ID NO:47) pentapeptide repeats and the EBP with elasticity (EBPE) having the Val-Pro-Gly-X$_{aa}$-Gly (VPGXG) (SEQ ID NO:46) pentapeptide repeats were replicated to have the same guest residue composition and ratio. The gene and amino acid sequences of the EBPs with different pentapeptide repeating units are shown in Table 1 and Table 2, respectively. For example, EBPE[G$_1$A$_3$F$_2$]$_{12}$ and EBPP[G$_1$A$_3$F$_2$]$_{12}$ show not only almost the same molar mass and but also the same combination of the fourth residue of the EBP pentapeptide repeating unit. They have different mechanical properties due to the difference in the third amino acid residue (Ala or Gly) of the pentapeptide repeating unit. Positively and negatively charged EBPs were constructed by introducing charged amino acids such as Lys, Asp, Glu, His, etc. as guest residues. In addition, in order to investigate the effect of the first amino acid ("Val" or "Ile") on temperature responsiveness and physical crosslinking of the triblock polypeptide, the first amino acid "Val" of the pentapeptide unit was substituted with "Ile", i.e., Ile-Pro-Ala-X$_{aa}$-Gly (IPAXG) (SEQ ID NO:49).

50 μL of each pair of oligonucleotides for encoding various EBPs at 2 μM concentration in T4 DNA ligase buffer were annealed by heating at 95° C. for 2 minutes and then slowly cooled down to the room temperature over 3 hours. The resulting dsDNA products have nonpalindromic, 2 bp, 3' overhangs. A total of 4 μg of the modified pET-21a(+) vector was digested with 15 U of BseRI in FastDigest buffer for 30 minutes at 37° C. The 5' ends were dephosphorylated with 10 U of CIP in NEB 3 buffer for 1 hour at 37° C. The restricted vector was purified using the PCR purification kit and was eluted in 40 μL of distilled deionized water. The dsDNA was inserted into the linearized and modified pET-21a(+) vector by incubating 90 pmol of the annealed dsDNA and 30 pmol of the vector in T4 DNA ligase buffer containing T4 DNA ligase at 16° C. for 30 minutes. The ligated vector was introduced into chemically transformed Top10 competent cells, and then plated on SOC (Super Optimal Broth with catabolite repression) plates supplemented with 50 μg/mL of ampicillin. The insert sequence was confirmed by DNA sequencing.

Two RBPs, RBP[Dros]$_n$ and RBP[m-Dros]$_n$, were derived from *Drosophila* exon 1. The RBP[Dros]$_n$ sequence was reported in previous studies with a repeating sequence of GGRPSDTYGAPGGGN (SEQ ID NO:53). But, in the present disclosure, two sequences were combined in the repeating unit to have same molecular weight as RBP[m-Dros]$_n$. The RBP[m-Dros]$_n$ was RBP[Dros]$_n$ modified with two repeating sequences of GGRPSDSYGAPGGGN (SEQ ID NO:54) and GGRPSSSYGAPGQGN (SEQ ID NO:55). The nucleotide and amino acid sequences of RBP[Dros]$_1$ and RBP[m-Dros]$_i$ are given in Table 3 and Table 4, respectively.

TABLE 3

Gene sequences of RBP libraries

| RBP | Gene Sequence |
|---|---|
| RBP[m-Dros]$_1$ (SEQ ID NO: 42) | GGC GGC CGT CCG TCA GAT TCT TAT GGC GCA CCG GGT GGG GGT AAT GGC GGC CGT CCA TCT TCG AGC TAT GGC GCA CCG GGC CAA GGT AAT |
| RBP[Dros]$_1$ (SEQ ID NO: 43) | GGG GCG CCG GGT GGT GGC AAC GGT GGT CGT CCG AGC GAT ACC TAC GGG GCG CCG GGT GGT GGC AAC GGT GGT CGT CCG AGC GAT ACC TAC |

TABLE 4

Amino acid sequences of RBP libraries

| RBP | Amino Acid Sequence |
|---|---|
| RBP[m-Dros]1 (SEQ ID NO: 44) | GGRPSDSYGAPGGGN GGRPSSSYGAPGQGN |
| RBP[Dros]1 (SEQ ID NO: 45) | GGRPSDTYGAPGGGN GGRPSDTYGAPGGGN |

Figure 1B:
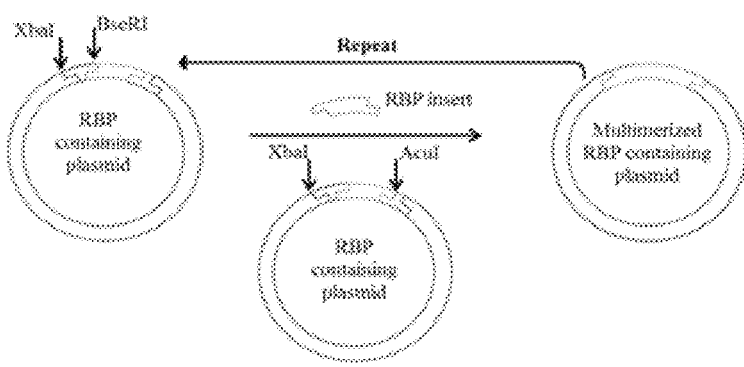
Figure 1C:
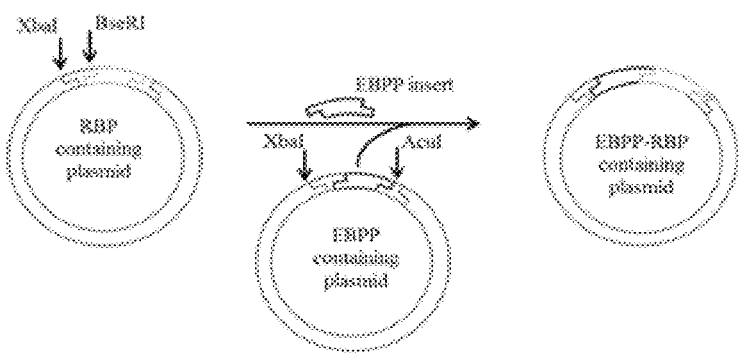
Figure 1D:
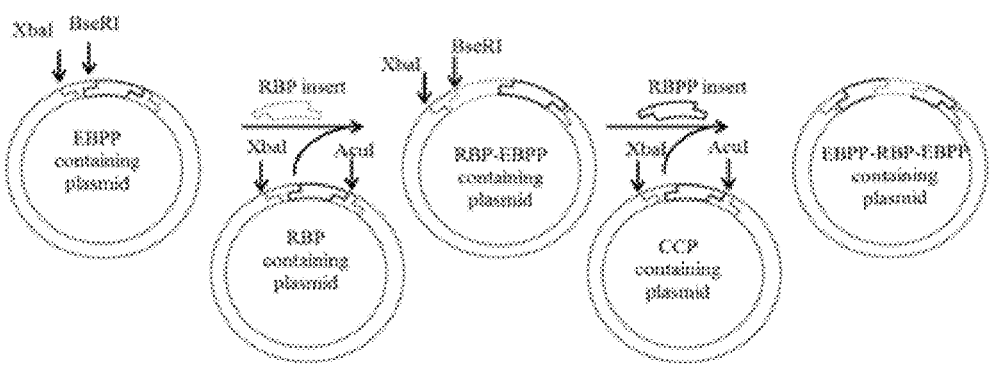

As shown in FIG. 1B, the RBP gene was multimerized up to 30 repeating units by RDL. A vector was prepared through double digestion by 15 U of BseRI and 10 U of XbaI and dephosphorylation by 10 U of CIP. For insertion, a total of 4 μg of monomer genes were digested with 10 U of XbaI and 15 U of AcuI in Outsmart buffer at 37° C. for 30 minutes. After the digestion, the reaction product was separated by agarose gel electrophoresis and purified using the PCR purification kit. Ligation was carried out by incubating 30 pmol of the purified insert with 30 pmol of the linearized vector in T4 DNA ligase buffer containing 1 U of T4 DNA ligase at 16° C. for 30 minutes. E. coli Top 10 competent cells were transformed with the ligated product and then spread on SOC plates supplemented with 50 μg/mL of ampicillin. The transformants were initially screened by diagnostic restriction endonuclease digests (restricted by XbaI and BamHI) and further confirmed by DNA sequencing.

Example 5. Expression/Purification and Characterization of RBP

The RBP[Dros]$_n$ and RBP[m-Dros]$_n$ gene containing plasmids were transformed into E. coli BL21 (DE3) cells. A single bacterial colony was inoculated into 10 mL of TB media (1st primary culture) containing 50 mg/mL ampicillin and incubated at 37° C. for overnight growth at 150 rpm. 400 mL of TB medium supplemented with 50 mg/mL ampicillin was inoculated with the 1st primary culture in a 2-L flask and incubated at 37° C. for 4 hours at 200 rpm. The 2nd primary culture was inoculated into 500 mL of CircleGrow containing trace elements in a 2-L flask and incubated at 37° C. and 200 rpm. Bacterial cells were harvested by centrifugation and cell pellets were resuspended in PBS. Cells lysate was obtained by sonicating the resuspended sample on an ice bath for 5 minutes at 50% power (10 seconds on with 20-second intervals).

RBP[Dros]$_n$ was purified by the ammonium sulfate precipitation and heating method as described in previous literatures with slight modifications. The sonicated sample was centrifuged at 16000 rpm for 30 minutes at 4° C. to remove insoluble cell debris and a PEI solution (0.5%) was added to the supernatant. Nucleic acid contaminants were separated by centrifuging at 16000 rpm for 15 minutes at 4° C. The clear soluble lysate was used for the purification of RBP[Dros]. The ammonium sulfate salt at final saturation of 30% was slowly added to the PEI-treated sample at 4° C. with stirring, mixed completely and kept for 20 minutes. Aggregated proteins were separated by centrifugation at 16000 rpm for 20 minutes at 4° C. and the pellet was resuspended in PBS. RBP[Dros]$_n$ was separated with 20% s ammonium sulfate by centrifuging under the same condition as described above. The supernatant was discarded and the pellet was resuspended in PBS. The sample was dialyzed in excess PBS to remove the ammonium sulfate salt. A high-purity product was obtained using the thermal stability of RBP[Dros]$_n$ and the sample was heated at 90° C. for 5 minutes with stirring which denatured the contaminated proteins. The RBP[Dros]$_n$ was maintained in solubilized state even under the high temperature condition. The denatured proteins were removed by centrifuging at 13000 rpm for 20 minutes at room temperature. The pellet was discarded and pure RBP[Dros]$_n$ existing in the supernatant was stored for further use.

For purification of the RBP[m-Dros]$_n$, the sonicated sample was centrifuged at 16000 rpm for 30 minutes at 4° C. The supernatant was discarded and the cell pellet was resuspended in 3-5 mL of PBS. The sample was heated at 65° C. for 20 minutes for complete solubilization and the heated sample was centrifuged at 16000 rpm for 15 minutes at room temperature to remove the contaminated proteins. The RBP[m-Dros]$_n$ remained in the supernatant because of its solubility at high temperature. The supernatant was cooled at 4° C. for 30 minutes and then cooled to −20° C. for 5 minutes to trigger the phase transition of the RBP[m-Dros]$_n$ which was visible due to increased turbidity. The aggregated proteins were separated by centrifugation at 16000 rpm for 10 minutes at 4° C. and the cell pellet was suspended in PBS at room temperature. The solubilization at high temperature and aggregation cycles at low temperature were continued for 3 more times to get purified proteins.

Purity and molecular weight were analyzed by SDS-PAGE for Coomassie-stained RBP[Dros]$_n$ and copper-stained RBP[m-Dros]$_n$. The phase transition behavior of the RBP[m-Dros]$_n$ was characterized by UV-visible spectrophotometry and dynamic light scattering (DLS). For the lower critical solution temperature, the 25 μM sample solution was heated to 50° C. and then optical density at 350 nm (OD$_{350}$) was measured from 50° C. to 10° C. as a function of temperature at a cooling rate of 1° C./min.

Figure 2A:
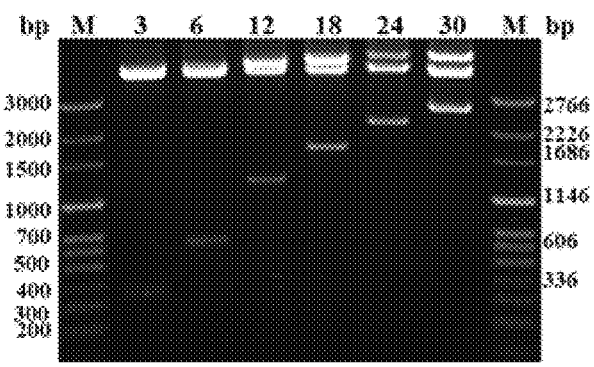
FIGS. 2A-2B shows the agarose gel electrophoresis images of FIG. 2A RBP[m-Dros]$_n$ and FIG. 2B RBP[Dros]$_n$ gene libraries according to the present disclosure. The left lane shows size markers and the expected size of each RBP[m-Dros]$_n$ gene is shown on the right side. The number of repeating units encoded by each gene is labeled above each lane.
Figure 2B:
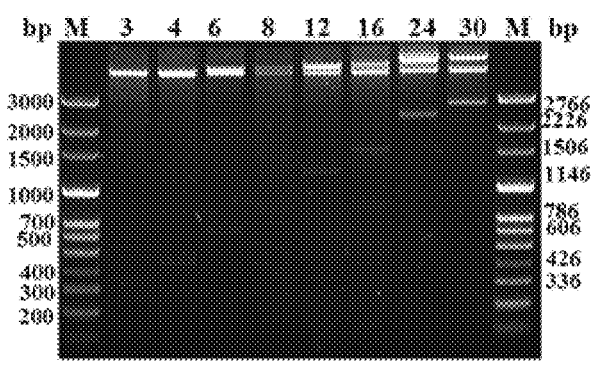
Figure 3A:
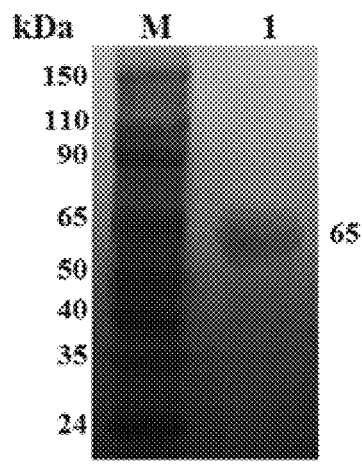
FIGS. 3A-3D shows the SDS-PAGE result of RBPs according to the present disclosure.
Figure 3B:
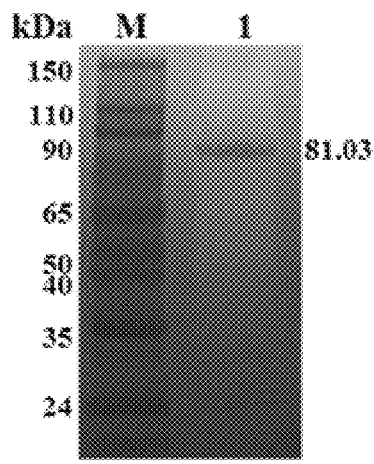
Figure 3C:
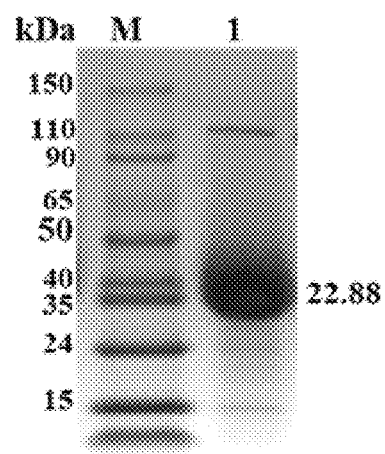

Through the agarose gel electrophoresis analysis, RBP [Dros]$_n$ and RBP[m-Dros]$_n$ gene libraries having various repeating units from 336 bp to 2766 bp were identified (FIG. 2A and FIG. 2B). FIGS. 3A-3C show the molecular weight of the Coomassie-stained RBP[m-Dros]$_{24}$, RBP[m-Dros]$_{30}$ and RBP[Dros]$_8$. The expected molecular weight of the RBP[m-Dros]$_n$ and RBP[Dros]$_n$ multimerized by RDL is shown in Table 5.

TABLE 5

Expected molecular weight of RBP[m-Dros]$_n$ and RBP[Dros]$_n$ multimerized by RDL

| RBP monoblock polypeptides | MW (kDa) |
|---|---|
| RBP[m-Dros]$_3$ | 8.48 |
| RBP[m-Dros]$_6$ | 16.59 |
| RBP[m-Dros]$_{12}$ | 32.81 |
| RBP[m-Dros]$_{24}$ | 65.26 |
| RBP[m-Dros]$_{30}$ | 81.48 |
| RBP[Dros]$_3$ | 8.44 |
| RBP[Dros]$_6$ | 16.50 |
| RBP[Dros]$_8$ | 21.30 |
| RBP[Dros]$_{12}$ | 32.63 |
| RBP[Dros]$_{16}$ | 43.39 |
| RBP[Dros]$_{24}$ | 64.90 |
| RBP[Dros]$_{30}$ | 81.03 |

Figure 3D:
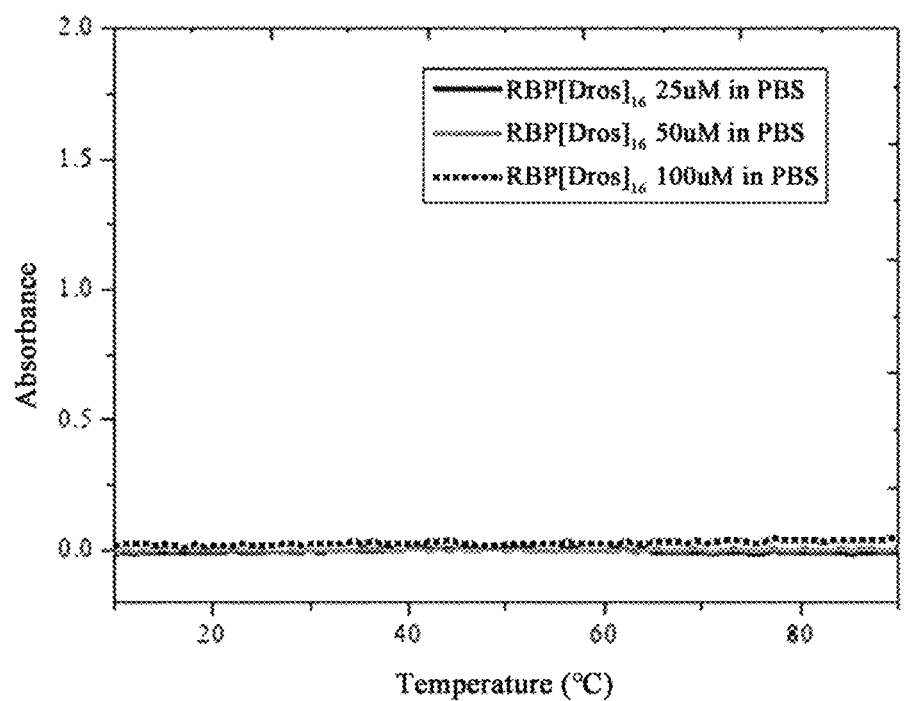
Figure 4A:
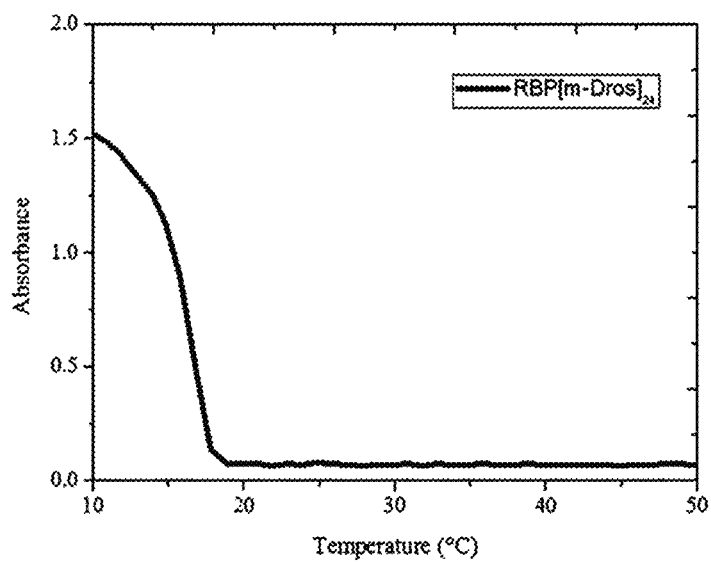
FIGS. 4A-4D shows a result of analyzing the characteristics of RBP[m-Dros]$_n$. The result of thermal profiling of FIG. 4A RBP[m-Dros]$_{24}$, FIG. 4B RBP[m-Dros]$_{30}$. The thermal profile data were collected by cooling the 25 µM solution of each block in PBS from 50° C. to 10° C. at a cooling rate of 1° C./min. The DLS measurement result of FIG. 4C RBP[m-Dros]$_{24}$ and FIG. 4D RBP[m-Dros]$_{30}$. The hydrodynamic radius (R$_h$) of each blocks (15 µM) at a scattering angle of 90° as a function of temperature was measured from 30° C. to 0° C.
Figure 4B:
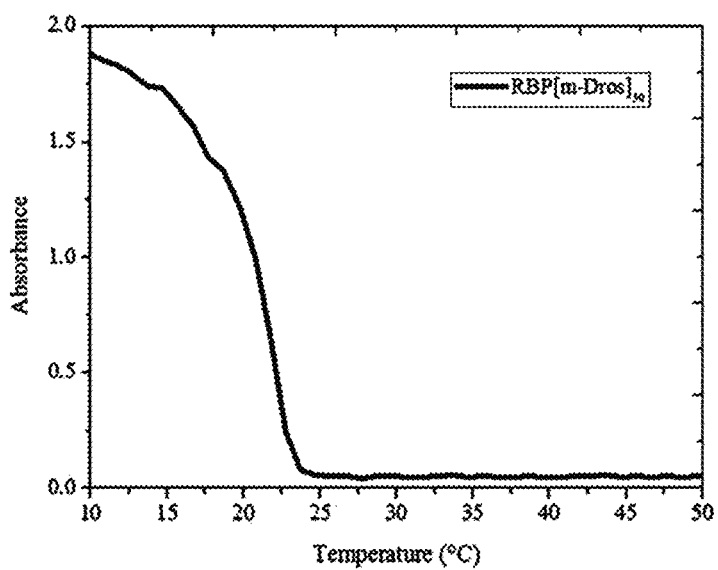
Figure 4C:
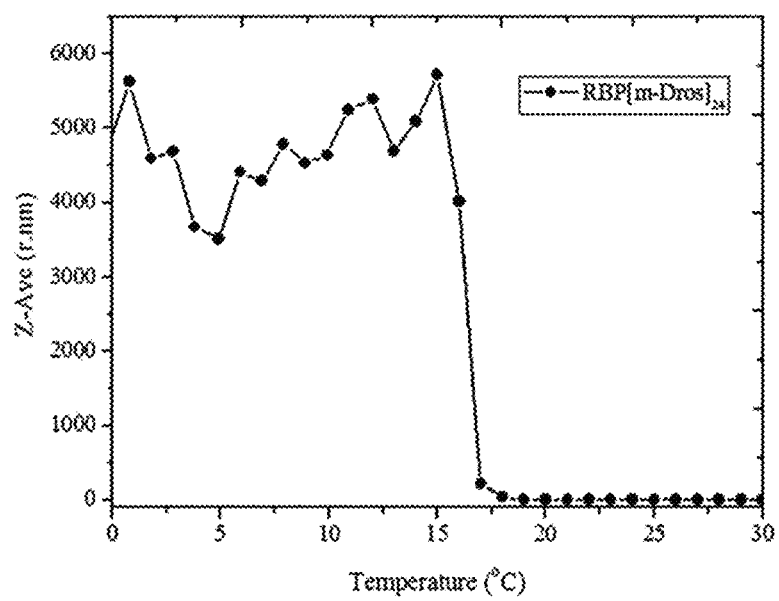
Figure 4D:
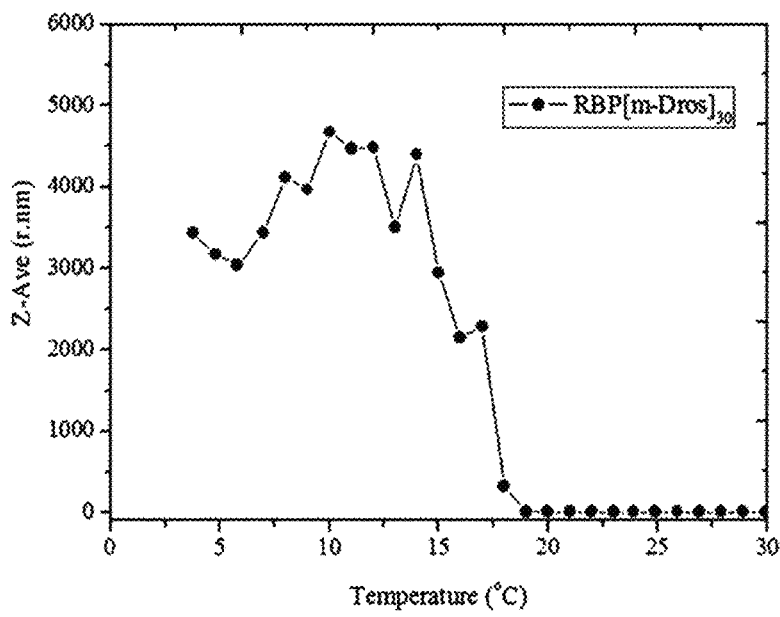

FIG. 3D shows the thermal profile of the RBP[Dros]$_{16}$. No transition was observed in the thermal profile of the RBP[Dros]$_{16}$ at different concentrations (25, 50 and 100 μM in PBS) over the range from 10° C. to 85° C. at a heating rate of 1° C./min. FIGS. 4A and 4B show the thermal transition behavior of the RBP[m-Dros]$_{24}$ and the RBP[m-Dros]$_{30}$, respectively, by measuring absorbance at 350 nm over the range from 50° C. to 10° C. at a cooling rate of 1° C./min. From FIG. 4C and FIG. 4D, it was confirmed that the RBP[m-Dros]$_{24}$ and the RBP[m-Dros]$_{30}$ were aggregated when the solution was cooled from 30° C. to 0° C. at a cooling rate of 1° C./min. That is to say, the RBP[m-Dros]$_{24}$ and the RBP[m-Dros]$_{30}$ showed varying UCST and cloud point depending on the block length of RBP[m-Dros]$_n$. Turbidity increased as the completely solubilized RBP[m-Dros]$_n$ was cooled below the UCST, which suggests aggregation. As reported previously, longer block lengths resulted in higher UCST.

Example 6. Synthesis and Expression of EBPP-RBPP Diblock Polypeptide Gene

As seen from FIG. 10, EBPP-RBP diblock genes were synthesized by inserting the EBPP gene into the RBP gene-containing plasmid. Two EBPP genes, EBPP [G$_1$A$_3$F$_2$]$_6$ and EBPP[G$_1$A$_3$F$_2$]$_{12}$, were fused with different block lengths of both [Dros] and [m-Dros]. For vector preparation, 4 μg of the plasmid was digested with 15 U of BseRI and 10 U of XbaI in FastDigest buffer for 30 minutes at 37° C. The 5' ends were dephosphorylated with 10 U of CIP in NEB 3 buffer for 1 hour at 37° C. The restricted vector was purified using the PCR purification kit. For insertion, the plasmid was doubly digested with 10 U of XbaI and 15 U of AcuI for 30 minutes at 37° C. The digested product was separated by agarose gel electrophoresis and purified using the PCR purification kit. Ligation was carried out by incubating 90 pmol of the purified insert and 30 pmol of the linearized vector in T4 DNA ligase buffer containing 1 U of T4 DNA ligase at 16° C. for 30 minutes. E. coli Top 10 competent cells were transformed with the ligated product and then spread on SOC plates supplemented with 50 μg/mL of ampicillin. All block lengths were checked by agarose gel electrophoresis after restriction by XbaI and AcuI and further confirmed by DNA sequencing.

For expression of fusion proteins, the pET-21a(+) vector containing EBPP-RBP polypeptides was transformed into E. coli BL21(DE3) cells. A single colony was inoculated into 50 mL of CircleGrow media in 250-mL flasks containing 50 μg/mL of ampicillin, and subsequently used to inoculate CircleGrow media in 2-L flasks. The flasks were incubated on a shaking incubator at 200 rpm and expression was induced by adding IPTG at a final concentration of 1 mM when the optical density (OD$_{600}$) reached 1.0. The cultures were harvested after 18 hours of incubation and the fusion proteins were purified by ITC. The cell pellets were resuspended in PBS, and the cells lysate was obtained by sonicating the samples (VC-505, Sonic and Materials Inc., Danbury, Connecticut) on an ice bath. The cells debris was separated by centrifugation at 16000 rpm for 15 minutes at 4° C. and the soluble lysate was transferred to a fresh tube. Then a PEI solution was added to a final concentration of 0.5% w/v and mixed well. Nucleic acid contaminants were separated by centrifuging at 16000 rpm for 15 minutes at 4° C. Sodium chloride was added at a final concentration of 3-4 M to the PEI-treated samples to trigger the phase transition of the fusion proteins. The aggregated fusion proteins were separated by centrifuging at 16000 rpm for 30 minutes at 40° C. The aggregated fusion proteins were resuspended in cold PBS, and the samples were centrifuged at 16000 rpm for 15 minutes at 4° C. to remove any remaining insoluble matter. This aggregation and resuspension process was repeated 4-5 times until an appropriate purity of the fusion proteins was obtained.

Example 7. Physicochemical Properties of EBPP-RBP Diblock Polypeptide

Figure 5A:
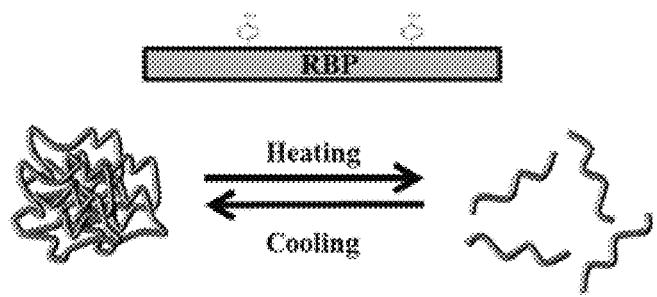
FIGS. 5A-5C schematically shows RBP[m-Dros]$_n$ and EBPP-RBP[m-Dros]$_n$ polypeptides with their transition behavior.
Figure 5B:
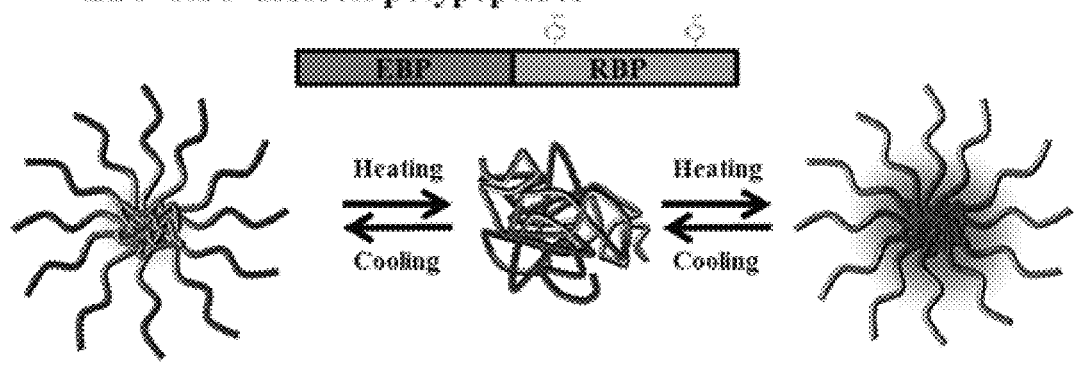

FIG. 5B schematically shows the EBPP-RBP diblock polypeptide with stimuli responsiveness, fused from the hydrophobic EBP and RBP[m-Dros], which reversibly forms a micelle structure. At low temperature, a core-shell micelle structure is formed due to the difference in hydrophobicity of the blocks. Below the LOST, the EBPP is solubilized whereas the RBP[m-Dros] is aggregated. The RBP[m-Dros] remains aggregated above the LOST of the EBPP, forming an aggregate as a whole. The aggregate consisting of the RBP[m-Dros] core and the EBPP shell forms a micelle structure again at high temperature of ~80° C. as the RBP[m-Dros] is solubilized above the UCST. The self-assembly from the EBPP-RBP[m-Dros] diblock to the micelle is reversible. The expected molecular weight and transition temperature (T$_t$) of EBPP[G$_1$A$_3$F$_2$]$_6$ or EBPP [G$_1$A$_3$F$_2$]$_{12}$ when fused with RBP[Dros]$_n$ or RBP[m-Dros]$_n$ of various lengths depending on the length of the hydrophobic block and the RBP[m-Dros]$_n$ are given in Table 6.

TABLE 6

Expected molecular weight and transition temperature of EBPP-RBP diblock peptide having different block lengths

| EBPP-RBP diblock polypeptides | MW (kDa) | T$_t$S |
|---|---|---|
| EBPP[G$_1$A$_3$F$_2$]$_6$-RBP[m-Dros]$_3$ | 23.55 | 44.5 |
| EBPP[G$_1$A$_3$F$_2$]$_6$-RBP[m-Dros]$_6$ | 31.66 | 48.9 |
| EBPP[G$_1$A$_3$F$_2$]$_6$-RBP[m-Dros]$_{12}$ | 47.88 | 47.9 |
| EBPP[G$_1$A$_3$F$_2$]$_6$-RBP[m-Dros]$_{24}$ | 80.32 | 55.4 |
| EBPP[G$_1$A$_3$F$_2$]$_{12}$-RBP[m-Dros]$_3$ | 38.61 | 36.62 |
| EBPP[G$_1$A$_3$F$_2$]$_{12}$-RBP[m-Dros]$_6$ | 46.72 | 33.21 |
| EBPP[G$_1$A$_3$F$_2$]$_{12}$-RBP[m-Dros]$_{12}$ | 62.94 | 31.49 |

TABLE 6-continued

Expected molecular weight and transition temperature of EBPP-RBP diblock peptide having different block lengths

| EBPP-RBP diblock polypeptides | MW (kDa) | $T_{tS}$ |
|---|---|---|
| EBPP[$G_1A_3F_2$]$_{12}$-RBP[m-Dros]$_{24}$ | 95.39 | 28.00 |
| EBPP[$G_1A_3F_2$]$_6$-RBP[Dros]$_3$ | 23.50 | N/A |
| EBPP[$G_1A_3F_2$]$_6$-RBP[Dros]$_6$ | 31.57 | N/A |
| EBPP[$G_1A_3F_2$]$_6$-RBP[Dros]$_{12}$ | 47.70 | N/A |
| EBPP[$G_1A_3F_2$]$_6$-RBP[Dros]$_{24}$ | 79.96 | N/A |
| EBPP[$G_1A_3F_2$]$_{12}$-RBP[Dros]$_3$ | 38.57 | N/A |
| EBPP[$G_1A_3F_2$]$_{12}$-RBP[Dros]$_6$ | 46.63 | N/A |
| EBPP[$G_1A_3F_2$]$_{12}$-RBP[Dros]$_{12}$ | 62.76 | N/A |
| EBPP[$G_1A_3F_2$]$_{12}$-RBP[Dros]$_{24}$ | 95.03 | N/A |

Figure 6A:
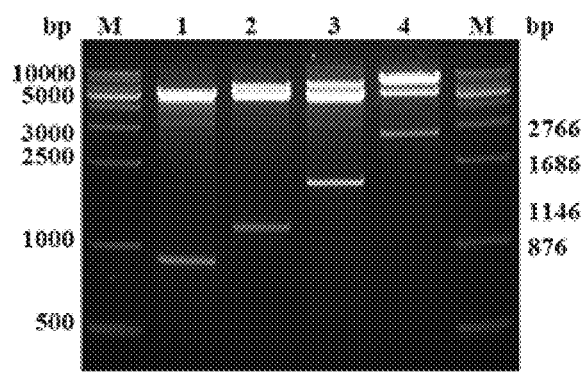
FIG. 6A and FIG. 6C are agarose gel and SDS-PAGE images of diblock polypeptides having EBPP[G$_1$A$_3$F$_2$]$_6$. Lane 1: RBP[m-Dros]$_3$-EBPP[G$_1$A$_3$F$_2$]$_6$, lane 2: RBP[m-Dros]$_6$-EBPP[G$_1$A$_3$F$_2$]$_6$, lane 3: RBP[m-Dros]$_{12}$-EBPP [G$_1$A$_3$F$_2$]$_6$, lane 4: RBP[m-Dros]$_{24}$-EBPP[G$_1$A$_3$F$_2$]$_6$.
Figure 6C:
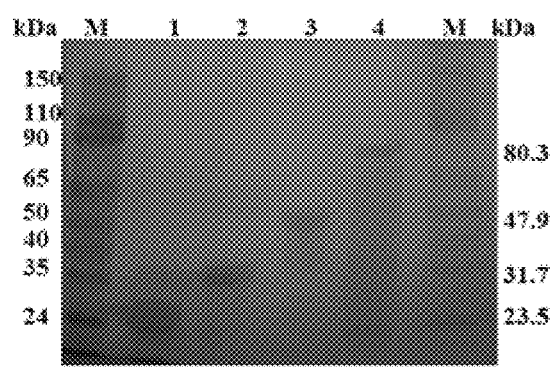
Figure 7A:
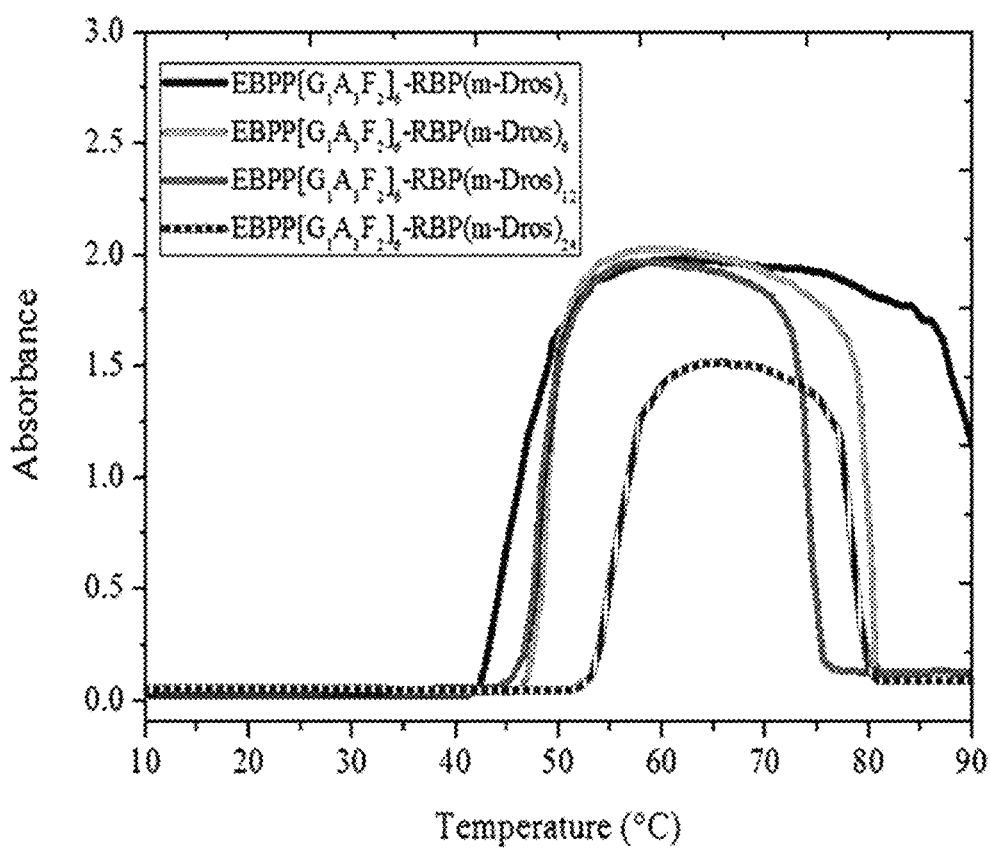
FIGS. 7A-7B shows a result of analyzing the characteristics of EBPP[G$_1$A$_3$F$_2$]$_6$ diblock polypeptides having RBP [m-Dros] in PBS (10 mM, pH 7.4). In the example of FIG. 7A, the thermal profile data were obtained by heating from 10° C. to 90° C. at a heating rate of 1° C./min. A micelle structure having RBP[m-Dros] as a core was formed below the LOST of EBPP[G$_1$A$_3$F$_2$]$_6$ and an aggregate was formed as a whole above the LOST of EBPP[G$_1$A$_3$F$_2$]$_6$. At ~80° C., all the diblock polypeptides except the EBPP[G$_1$A$_3$F$_2$]$_6$-RBP[m-Dros]$_3$ reversibly formed micelles due to solubilization of RBP[m-Dros] above the UCST.

The molecular weight of the diblock polypeptide varied from 23.55 to 95.03 kDa. FIGS. 6A and 6C show the gene lengths and protein purification of the diblocks containing [$G_1A_3F_2$]$_6$ (lane 1: RBP[m-Dros]$_3$-EBPP[$G_1A_3F_2$]$_6$, lane 2: RBP[m-Dros]$_6$-EBPP[$G_1A_3F_2$]$_6$, lane 3: RBP[m-Dros]$_{12}$-EBPP[$G_1A_3F_2$]$_6$, lane 4: RBP[m-Dros]$_{24}$-EBPP[$G_1A_3F_2$]$_6$). FIG. 7A shows the thermal profile of the diblock polypeptides containing [$G_1A_3F_2$]$_6$. The diblock polypeptides except EBPP[$G_1A_3F_2$]$_6$-RBP[m-Dros]$_3$ show three stages of thermal transition: micelle formation, aggregation and micelle structure formation. In the first stage, the hydrophobic RBP[m-Dros]$_3$ is aggregated at low temperature to form a core, whereas the EBPP remains soluble and serves as a shell. As the temperature is increased above the LOST of the EBPP, an aggregate is formed as a whole. In the third stage, absorbance is decreased rapidly as the temperature is increased above 70° C. and a reversible micelle structure is formed as the RBP[m-Dros] is solubilized.

Figure 7B:
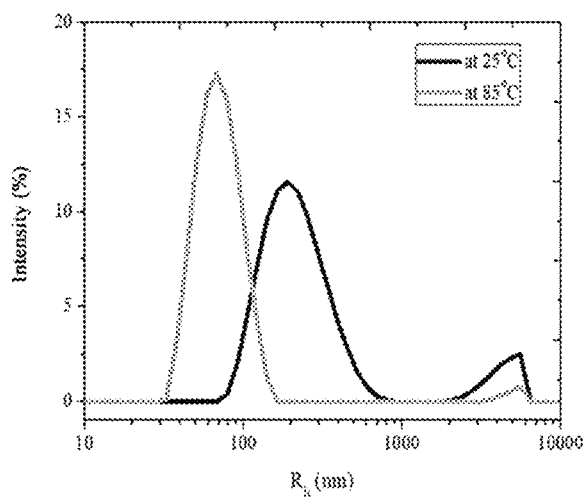

At this temperature, the EBPP[$G_1A_3F_2$]$_6$ serves as a core and the RBP[m-Dros]$_{24}$ serves as a shell. Whereas the UCST of the monoblock is −18° C., the fusion of EBPP[$G_1A_3F_2$]$_6$ and RBP[m-Dros]$_{24}$ resulted in increased UCST because the aggregated state is maintained until the thermal transition of the EBPP[$G_1A_3F_2$]$_6$. For the EBPP[$G_1A_3F_2$]$_6$-RBP[m-Dros]$_3$, a micelle was not formed because the effect of the EBPP[$G_1A_3F_2$]$_6$ was dominant throughout the temperature range due to the small molecular weight. FIG. 7B shows a result of measuring the size of the EBPP[$G_1A_3F_2$]$_6$-RBP[m-Dros]$_{24}$ at low and high temperatures. The $R_h$ was 68 mm at 25° C., but 34 mm at 85° C. That is to say, the micelle structure and size of the diblock polypeptide could be changed reversibly by controlling the temperature.

Figure 8A:
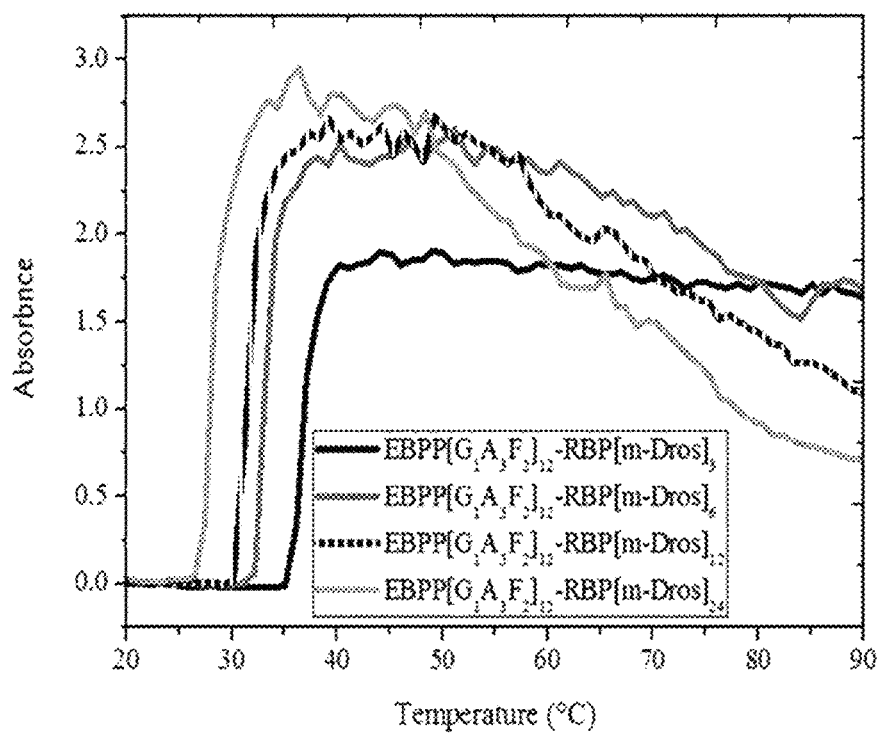
FIGS. 8A-8B shows the thermal profiles of RBP[m-Dros]$_n$.

FIG. 8A shows the thermal profile of the EBPP[$G_1A_3F_2$]$_{12}$-RBP[m-Dros]$_n$ diblocks. All the diblock polypeptides containing EBPP[$G_1A_3F_2$]$_{12}$ were in solubilized state below the LOST of the EBPP and remained in aggregated state above the temperature. Unlike when the length of the EBPP was shorter, micelle formation was not observed at low and high temperatures. This result suggests that the RBP[m-Dros] is greatly affected by the hydrophobic block at low and high temperatures. The effect of the EBPP[$G_1A_3F_2$]$_{12}$ block was dominant throughout the temperatures and the UCST of the RBP[m-Dros] was not observed.

Example 8. Synthesis and Expression of EBPP-RBP-EBPP Triblock Polypeptide Gene

EBPP-RBP-EBPP triblock peptides were synthesized in two steps. In the first step, a RBP-EBPP block copolymer was formed by inserting the RBP gene into an EBPP-containing plasmid. In the second step, the EBPP gene was inserted into the RBP-EBPP-containing plasmid. For vector preparation, 4 μg of the plasmid was digested with 15 U of BseRI and 10 U of XbaI in FastDigest buffer for 30 minutes at 37° C. The 5' ends were dephosphorylated with 10 U of CIP in NEB 3 buffer for 1 hour at 37° C. The restricted vector was purified using the PCR purification kit. For insertion, the plasmid was doubly digested with 10 U of XbaI and 15 U of AcuI for 30 minutes at 37° C. The digested product was separated by agarose gel electrophoresis and purified using the PCR purification kit. Ligation was carried out by incubating 90 pmol of the purified insert and 30 pmol of the linearized vector in T4 DNA ligase buffer containing 1 U of T4 DNA ligase at 16° C. for 30 minutes. *E. coli* Top 10 competent cells were transformed with the ligated product and then spread on SOC plates supplemented with 50 μg/mL of ampicillin. Triblock polypeptides with different EBP lengths and RBP genes were synthesized and all block lengths were checked by agarose gel electrophoresis after restriction by XbaI and AcuI and further confirmed by DNA sequencing. Then, the expression of fusion proteins was conducted in the same manner as in Example 6.

Example 9. Physicochemical Properties of EBPP-RBP-EBPP Triblock Polypeptide

Figure 5C:
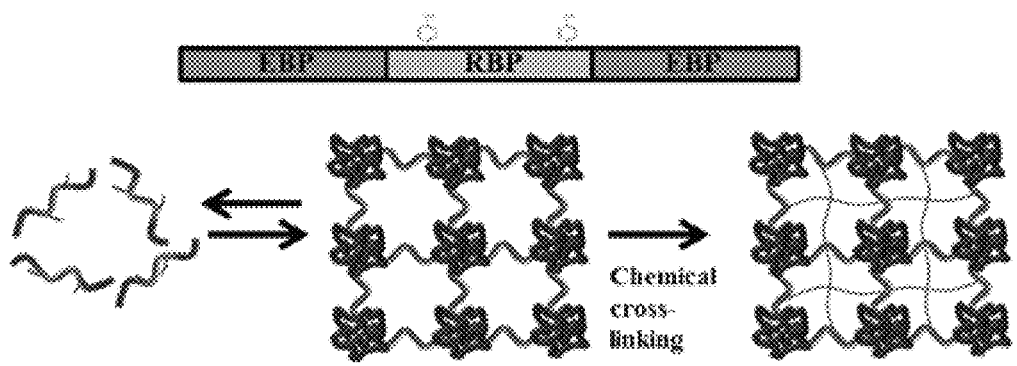

FIG. 5C schematically shows the hydrogel consisting of the EBPP-RBP-EBPP triblock polypeptide. It consists of the RBP[m-Dros] middle block and EBPP end blocks. The triblock polypeptide is completely soluble at low temperature and undergoes transition to a physically crosslinked network above the LOST of the EBPP. This self-assembly of the triblock polypeptide can occur reversibly depending on temperature change.

Under physiological conditions and above the $T_t$, the hydrophobic EBPP block self-assembled with the hydrophilic RBP middle block containing the tyrosine residues to form a physically crosslinked hydrogel. The mechanical properties of the physically crosslinked hydrogel was enhanced by the chemical crosslinkages of the tyrosine residues on the RBP block. The expected molecular weight and transition temperature ($T_t$) depending on the lengths of the hydrophobic block and the RBP[m-Dros]$_n$ when EBPP [$G_1A_3F_2$]$_{12}$ or EBPP[$G_1A_3F_2$]$_{24}$ is fused with RBP[m-Dros]$_n$ of various lengths are given in Table 7. In addition, in order to confirm the effect of physical crosslinking, EBPP or EBPPI libraries differing only in the first amino acid residue of the pentapeptide repeating unit ("Val" or "Ile") were fused with the same RBP[m-Dros] block.

TABLE 7

Expected molecular weight and transition temperature of EBPP(I)-RBP-EBPP(I) triblock peptides having different block lengths

| EBPP-RBP-EBPP triblock polypeptides | MW (kDa) | $T_{tS}$ |
|---|---|---|
| EBPPI[$G_1A_3F_2$]$_{12}$-RBP[m-Dros]$_6$-EBPPI[$G_1A_3F_2$]$_{12}$ | 78.9 | 14.5 |
| EBPP[$G_1A_3F_2$]$_{12}$-RBP[m-Dros]$_6$-EBPP[$G_1A_3F_2$]$_{12}$ | 76.8 | 29.74 |
| EBPP[$G_1A_3F_2$]$_{24}$-RBP[m-Dros]$_6$-EBPP[$G_1A_3F_2$]$_{24}$ | 137.1 | 25.59 |
| EBPP[$G_1A_3F_2$]$_{12}$-RBP[m-Dros]$_{12}$-EBPP[$G_1A_3F_2$]$_{12}$ | 93.1 | 27.86 |
| EBPP[$G_1A_3F_2$]$_{24}$-RBP[m-Dros]$_{12}$-EBPP[$G_1A_3F_2$]$_{24}$ | 153.3 | 23.10 |

The transition temperature was decreased as the EBPP [$G_1A_3F_2$] block length was increased. In particular, the triblock polypeptides having EBPPI libraries showed much lower transition temperatures ($T_t$) than the triblock polypeptides of the same block lengths having EBPP libraries. That is to say, the LOST of EBPPI[$G_1A_3F_2$]$_{12}$-RBP[m-Dros]$_6$-

EBPPI[G₁A₃F₂]₁₂ was much lower than that of the EBPP [G₁A₃F₂]₁₂-RBP[m-Dros]₆-EBPP[G₁A₃F₂]₁₂ triblock polypeptide of the same block length but having EBPP library. Such a significant decrease in $T_t$ is due to the substitution of "Val" in the first position of the pentapeptide repeat with the relatively more hydrophobic "Ile".

Figure 6B:
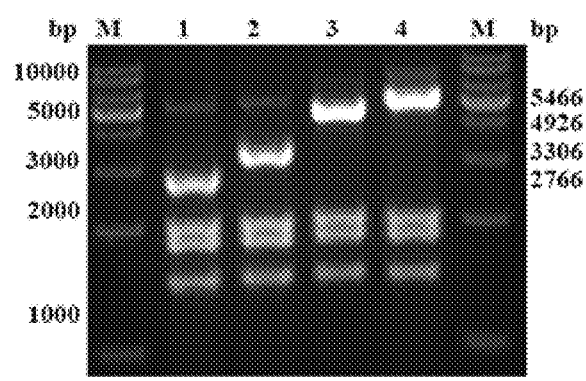
FIG. 6B and FIG. 6D are agarose gel and SDS-PAGE images of triblock polypeptides. Lane 1: EBPP[G$_1$A$_3$F$_2$]$_{12}$-RBP[m-Dros]$_6$-EBPP[G$_1$A$_3$F$_2$]$_{12}$, lane 2: EBPP[G$_1$A$_3$F$_2$]$_{12}$-RBP[m-Dros]$_{12}$-EBPP[G$_1$A$_3$F$_2$]$_{12}$, lane 3: EBPP[G$_1$A$_3$F$_2$]$_{24}$-RBP [m-Dros]$_6$-EBPP[G$_1$A$_3$F$_2$]$_{24}$, lane 4: EBPP[G$_1$A$_3$F$_2$]$_{24}$-RBP [m-Dros]$_{12}$-EBPP[G$_1$A$_3$F$_2$]$_{24}$. Lane (M) shows size markers and the expected molecular weight is labeled on the right side.
Figure 6D:
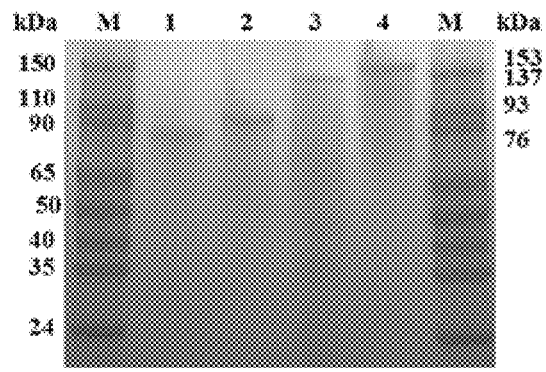
Figure 8B:
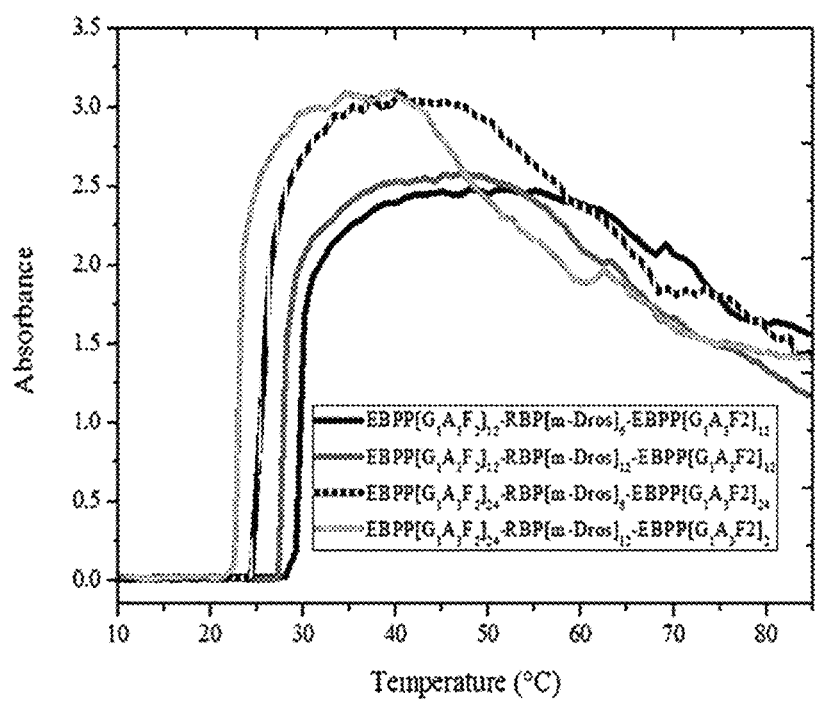

FIGS. 6B and 6D show the gene length and protein purification results for the [G₁A₃F₂]₆-containing triblocks (lane 1: EBPP[G₁A₃F₂]₁₂-RBP[m-Dros]₆-EBPP[G₁A₃F₂]₁₂, lane 2: EBPP[G₁A₃F₂]₁₂-RBP[m-Dros]₁₂-EBPP[G₁A₃F₂]₁₂, lane 3: EBPP[G₁A₃F₂]₂₄-RBP[m-Dros]₆-EBPP[G₁A₃F₂]₂₄, lane 4: EBPP[G₁A₃F₂]₂₄-RBP[m-Dros]₁₂-EBPP[G₁A₃F₂]₂₄). And, FIG. 8B shows the thermal profile for the EBPP[G₁A₃F₂]₁₂-RBP[m-Dros]ₙ-EBPP[G₁A₃F₂]₁₂ triblock polypeptide. The thermal profile pattern of the triblock polypeptide was similar to that of the diblock polypeptide where the effect of the EBPP [G₁A₃F₂]₁₂ block was dominant throughout all the temperatures.

Figure 9A:
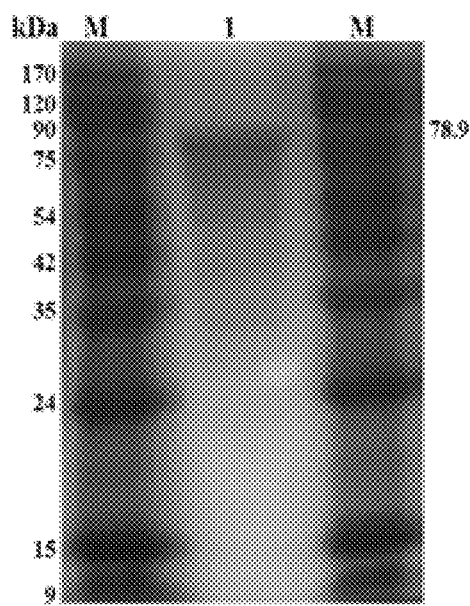
FIG. 9A illustrates an example of copper-stained SDS-PAGE gel (15%) and FIG. 9B illustrates an example of the thermal profile images of the EBPPI[G$_1$A$_3$F$_2$]$_{12}$-RBP[m-Dros]$_6$-EBPPI[G$_1$A$_3$F$_2$]$_{12}$ triblock polypeptide. Lane M: size marker, lane 1: triblock polypeptide. The thermal profile data were measured in PBS (10 mM, pH 7.4) with a sample concentration of 25 µM as a function of temperature while heating from 5° C. to 80° C. at a heating rate of 1° C./min.
Figure 9B:
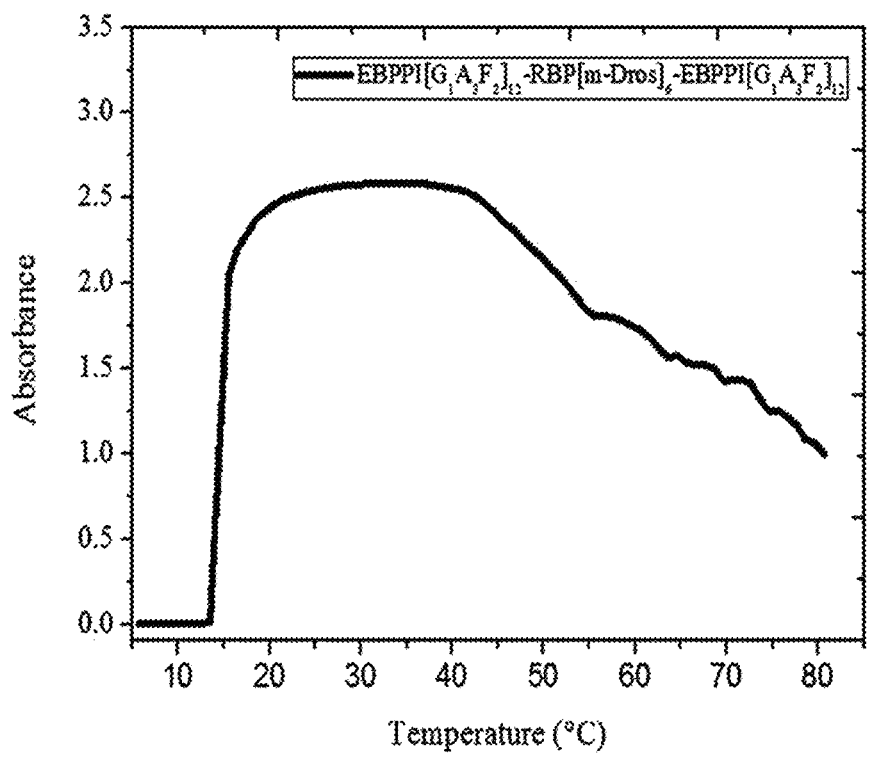
Figure 10A:
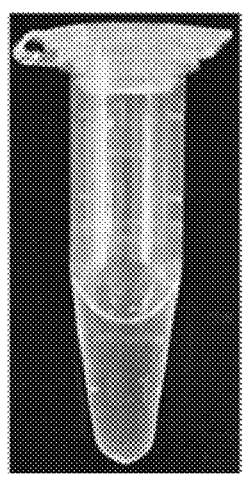
FIGS. 10A-10D shows the photographic images of EBPP [G$_1$A$_3$F$_2$]$_{12}$-RBP[m-Dros]$_6$-EBPP[G$_1$A$_3$F$_2$]$_{12}$ in 10 mM PBS at pH 7.4 as a function of temperature when sequentially incubated at 4° C.
Figure 10B:
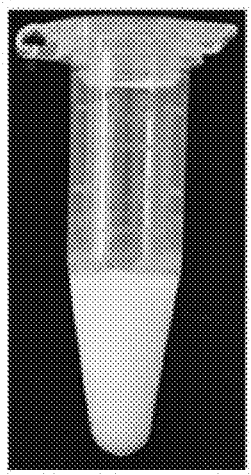
Figure 10C:
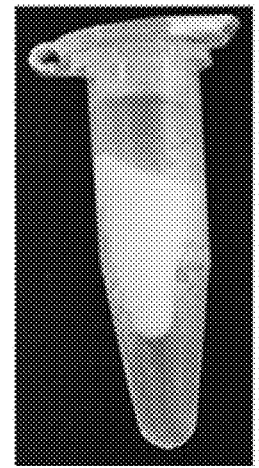
Figure 10D:
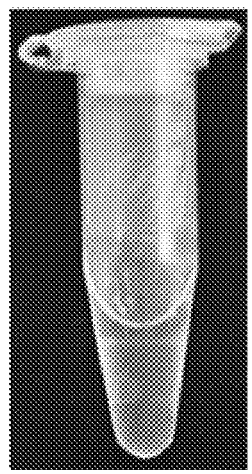

FIG. 9 shows the purity and characteristics of the triblock polypeptides having EBPPI libraries (Ile-Pro-Ala-$X_{aa}$-Gly) for investigating the effect of substitution of "Val" at the first position of the pentapeptide repeat with "Ile" with regard to the physical crosslinking of the hydrogel. FIG. 9A a single band for EBPPI[G₁A₃F₂]₁₂-RBP[m-Dros]₆-EBPPI [G₁A₃F₂]₁₂ in SDS-PAGE gel. FIG. 9B shows the thermal profile at 25 μM concentration in PBS, showing complete dissolution below the $T_t$ and rapid aggregation above the LOST.

FIG. 10 shows the photographic images for the reversible sol-gel transition behavior of EBPP[G₁A₃F₂]₁₂-RBP[m-Dros]₆-EBPP[G₁A₃F₂]₁₂ in 10 mM PBS at pH 7.4. The triblock polypeptide was in solubilized state below the $T_t$ of EBPP and turned into an aggregate and formed a physically crosslinked network as the temperature was increased. The aggregated was dissolved again as the temperature was lowered. This result confirms the reversibility of the physically crosslinked hydrogel.

Example 10. Rheological Measurement of EBPP-RBP-EBPP Triblock Polypeptide

Various concentrations of EBPP-RBP-EBPP polypeptide solutions were prepared using phosphate-buffered saline (PBS, pH 7.4) and subjected to dynamic-shear rheological test to measure the elastic modulus (G'), loss modulus (G"), complex shear modulus (G*), complex viscosity (η*) and loss angle (δ) as functions of temperature and frequency. The G' characterizes the elastic behavior of a material while the G" characterizes its viscous behavior. G* and η* represent the frequency-dependent stiffness and the frequency-dependent viscous drag of a viscoelastic liquid or solid, respectively. The loss angle (δ) is a relative measure of viscous to elastic properties (Newtonian viscous fluid: δ=90°; elastic solid: δ=0°). A metal solvent trap under fully hydrating conditions was used to prevent solvent evaporation over temperatures ranging from 10° C. to 40° C. Dynamic frequency sweep measurements were performed in the linear viscoelastic regime at different temperatures, as confirmed by independent strain sweep tests (strain sweep range: 0.2-20%, angular frequency: 0.1, 1.0 or 10 rad/s). The angular frequency ranged from 1.0 to 100 rad/s, both at 10° C. (below $T_t$) and 40° C. (above $T_t$) for the frequency sweep tests. The temperature sweep tests were executed with 2% strain at 1 rad/s over a temperature range of 10° C. to 45° C. with one-minute duration per degree for forward heating and reverse cooling measurements to examine the reversibility of their rheological and mechanical properties. All measurements were made 3 times to ensure reproducibility.

Figure 11A:
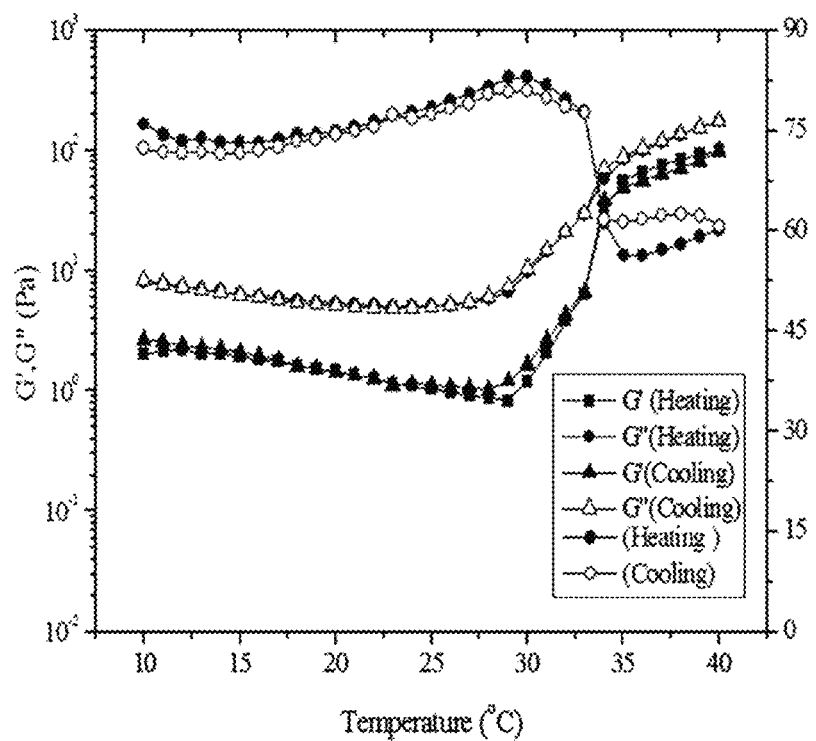
FIGS. 11A-11B shows a result of oscillatory rheological measurement for 35 wt % of EBPP[G$_1$A$_3$F$_2$]$_{12}$-RBP[m-Dros]$_{12}$-EBPP[G$_1$A$_3$F$_2$]$_{12}$ in 10 mM PBS at pH 7.4. The rheological behavior is shown FIG. 11A as a function of temperature at a heating rate of 1° C./min (strain 2%, 1 rad/s) and in FIG. 11B as a function of frequency (strain 2%, 10° C.).
Figure 11B:
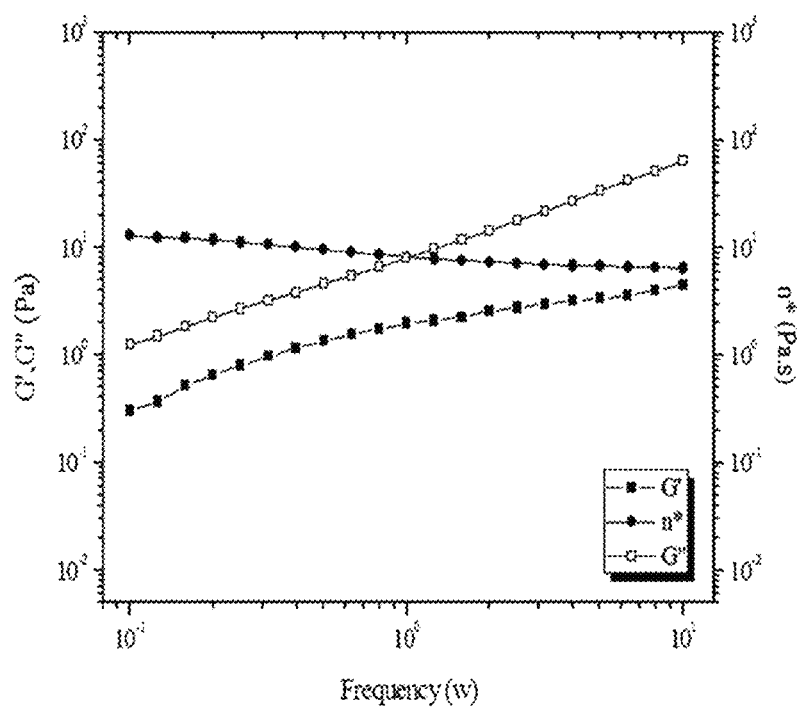
Figure 12A:
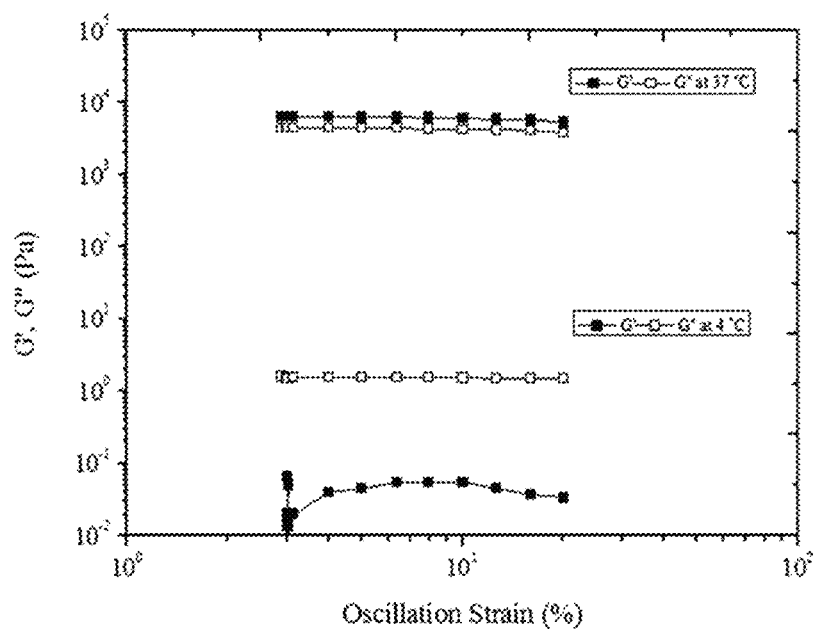
FIGS. 12A-12D shows a result of oscillatory rheological measurement for 25 wt % of EBPPI[G$_1$A$_3$F$_2$]$_{12}$-RBP[m-Dros]$_6$-EBPPI[G$_1$A$_3$F$_2$]$_{12}$ in PBS (10 mM, pH 7.4).
Figure 12B:
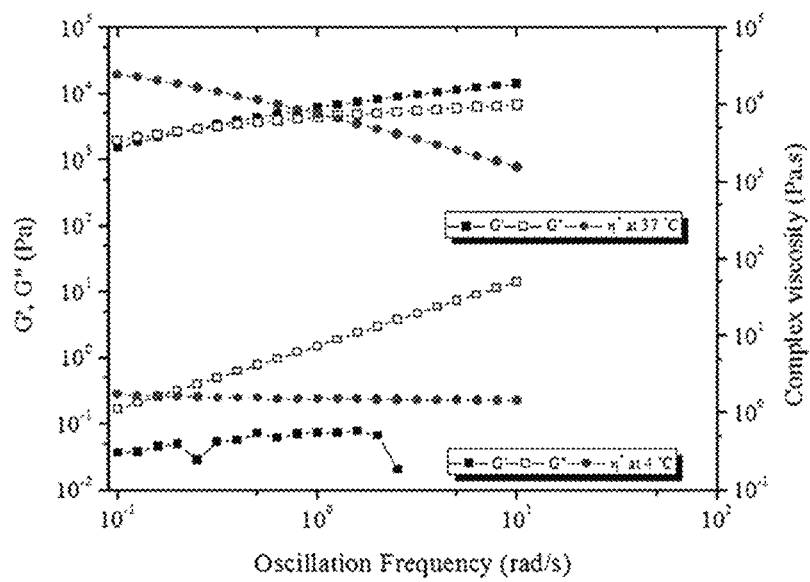
Figure 12C:
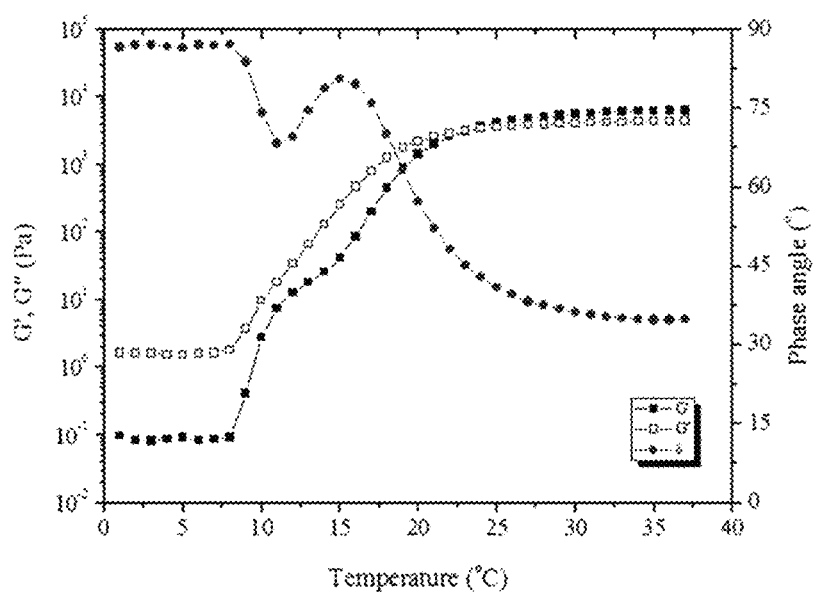
Figure 12D:
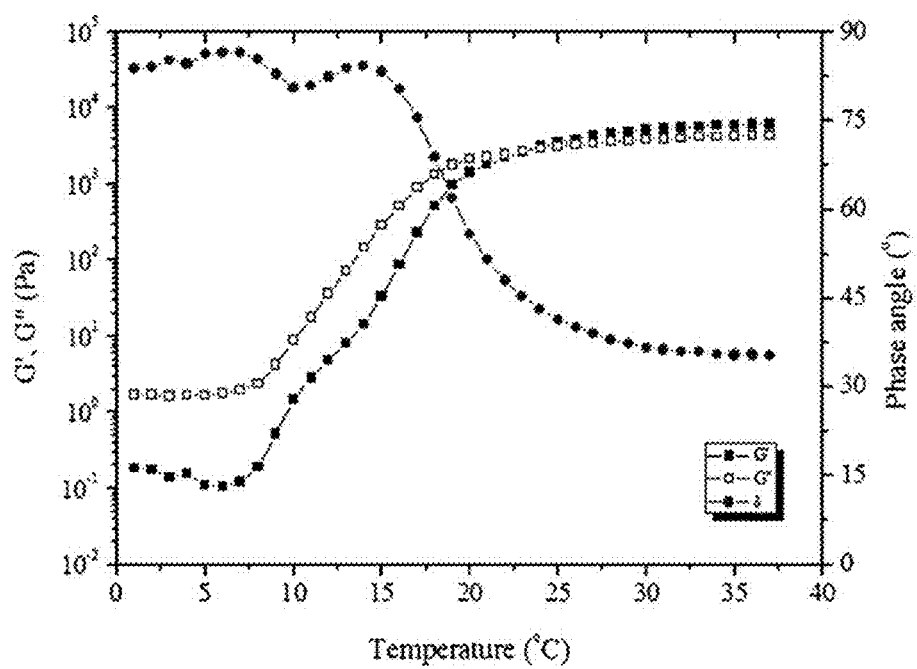

FIG. 11 shows the rheological measurement result of EBPP[G₁A₃F₂]₁₂-[RBP]₁₂-EBPP[G₁A₃F₂]₁₂ in 10 mM PBS buffer at pH 7.4. The rheological properties and thermal reversibility were measured from 10° C. to 40° C. at 1° C./min as shown in FIG. 11A. At 37° C., the loss angle (δ) was 57° and the values of G' and G" were approximately 76 Pa and 118. No physical crosslinking was observed as reflected by the absence of a crossover point in G' and G". FIG. 11B shows the frequency-dependent rheological behavior which showed the frequency dependence on G' and G" with no crossover point.

FIG. 12 shows rheological measurement result of 25 wt % EBPPI[G₁A₃F₂]₁₂-[m-RBP]₆-EBPP[G₁A₃F₂]₁₂ in 10 mM PBS buffer at pH 7.4. FIG. 12A shows higher G' at lower and higher temperatures than 37° C. FIG. 12B shows frequency-dependent G' and G" having a crossover point at 1 rad/s, suggesting that the polypeptide is a viscoelastic solid above the $T_t$ of EBPPI. FIGS. 12C and 12D show the measurement result as a function of temperature from 1 to 40° C. at a heating and cooling rate of 1° C./min. The triblock polypeptide having EBPPI libraries, wherein the "Val" at the first position of the pentapeptide repeat was substituted with "Ile", showed a modulus crossover point at 23° C., which clearly reveals gelation during thermal transition. This gelation was reversible as the temperature was decreased. The G' and G" values of the polypeptide below and above the crossover point were much higher for EBPPI[G₁A₃F₂]₁₂-[m-RBP]₆-EBPPI[G₁A₃F₂]₁₂ than for EBPP[G₁A₃F₂]₁₂-[m-RBP]₁₂-EBPP[G₁A₃F₂]₁₂, which suggests that the "Ile" in the pentapeptide repeating unit improves physical crosslinking by enhancing hydrophobicity.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A resilin-based polypeptide (RBP) exhibiting a phase transition behavior, which consists of the amino acid sequence of SEQ ID NO: 44.

2. The resilin-based polypeptide (RBP) according to claim 1, which is encoded by the polynucleotide sequence of SEQ ID NO: 42.

3. A diblock polypeptide with a temperature responsiveness, represented by Formula 1, which consists of:
   a resilin-based polypeptide block; and
   an elastin-based polypeptide block exhibiting a phase transition behavior, which is connected to one end of the resilin-based polypeptide block:
   [Formula 1]
   [hydrophobic EBP]$_m$-[RBP]$_n$
   wherein
   n or m is independently an integer 1 or greater,
   the [RBP] is a resilin-based polypeptide block consisting of the amino acid sequence of SEQ ID NO: 44, and
   the [hydrophobic EBP] is an elastin-based polypeptide block selected from the group consisting of:
   VPGXG VPGXG VPGXG VPGXG VPGXG VPGXG of SEQ ID NO: 1,
   VPAXG VPAXG VPAXG VPAXG VPAXG VPAXG of SEQ ID NO: 2, and
   IPAXG IPAXG IPAXG IPAXG IPAXG IPAXG of SEQ ID NO: 3; and
   wherein:
   i) when the [hydrophobic EBP] is the elastin-based polypeptide block of SEQ ID NO: 1, each X of the repeating pentapeptide consists of:
      A (Ala), G (Gly) and I (Ile) at a ratio of 1:4:1;
      K (Lys), G (Gly) and I (Ile) at a ratio of 1:4:1;
      D (Asp), G (Gly) and I (Ile) at a ratio of 1:4:1;
      E (Glu), G (Gly) and I (Ile) at a ratio of 1:4:1; or
      G (Gly), A (Ala) and F (Phe) at a ratio of 1:3:2;
   ii) when the [hydrophobic EBP] is the elastin-based polypeptide block of SEQ ID NO: 2, each X of the repeating pentapeptide consists of:
      G (Gly), A (Ala) and F (Phe) at a ratio of 1:3:2;
      K (Lys), A (Ala) and F (Phe) at a ratio of 1:3:2;
      D (Asp), A (Ala) and F (Phe) at a ratio of 1:3:2;
      K (Lys) and F (Phe) at a ratio of 3:3;
      D (Asp) and F (Phe) at a ratio of 3:3;
      H (His), A (Ala) and I (Ile) at a ratio of 3:2:1;
      H (His) and G (Gly) at a ratio of 5:1; or
      G (Gly), C (Cys) and F (Phe) at a ratio of 1:3:2; and
   iii) when the [hydrophobic EBP] is the elastin-based polypeptide block of SEQ ID NO: 3, each X of the repeating pentapeptide consists of:
      G (Gly), A (Ala) and F (Phe) at a ratio of 1:4:1; or
      G (Gly), A (Ala) and F (Phe) at a ratio of 1:3:2.

4. The diblock polypeptide with a temperature responsiveness according to claim 3, wherein when the [hydrophobic EBP] is a [VPGXG VPGXG VPGXG VPGXG VPGXG VPGXG] block of SEQ ID NO: 1, the [hydrophobic EBP] is SEQ ID NO: 23, SEQ ID NO: 25, SEQ ID NO: 27, SEQ ID NO: 29, or SEQ ID NO: 31.

5. The diblock polypeptide with a temperature responsiveness according to claim 3, wherein when the [hydrophobic EBP] is a [VPAXG VPAXG VPAXG VPAXG VPAXG VPAXG] block of SEQ ID NO: 2, the [hydrophobic EBP] is SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39.

6. The diblock polypeptide with a temperature responsiveness according to claim 3, wherein when the [hydrophobic EBP] is an [IPAXG IPAXG IPAXG IPAXG IPAXG IPAXG] block of SEQ ID NO: 3, the [hydrophobic EBP] is SEQ ID NO: 40 or SEQ ID NO: 41.

7. The diblock polypeptide with a temperature responsiveness according to claim 3, wherein the diblock polypeptide undergoes a dynamic change in response to temperature, and wherein
   a [RBP] block core-[hydrophobic EBP] block shell micelle structure is formed through self-assembly at or below the lower critical solution temperature of the [hydrophobic EBP],
   an aggregate is formed at or above the lower critical solution temperature of the [hydrophobic EBP], and
   a [hydrophobic EBP] block core-[RBP] block shell micelle structure is formed at or above the upper critical solution temperature of the [RBP].

8. The diblock polypeptide with a temperature responsiveness according to claim 7, wherein the dynamic change is reversible in response to temperature.

9. A drug delivery composition comprising the diblock polypeptide according to claim 3.

10. A triblock polypeptide with a temperature responsiveness, represented by Formula 2, which consists of:
    a resilin-based polypeptide block; and
    elastin-based polypeptide blocks exhibiting a phase transition behavior, which are connected to both ends of the resilin-based polypeptide block:

[Formula 2]
[hydrophobic EBP]$_m$-[RBP]$_n$-[hydrophobic EBP]$_m$
wherein
n or m is independently an integer 1 or greater,
the [RBP] is a resilin-based polypeptide block consisting of the amino acid sequence of SEQ ID NO: 44, and
the [hydrophobic EBP] is an elastin-based polypeptide block selected from the group consisting of:
VPGXG VPGXG VPGXG VPGXG VPGXG VPGXG of SEQ ID NO: 1,
VPAXG VPAXG VPAXG VPAXG VPAXG VPAXG of SEQ ID NO: 2, and
IPAXG IPAXG IPAXG IPAXG IPAXG IPAXG of SEQ ID NO: 3; and
wherein:
i) when the [hydrophobic EBP] is the elastin-based polypeptide block of SEQ ID NO: 1, each X of the repeating pentapeptide consists of:
  A (Ala), G (Gly) and I (Ile) at a ratio of 1:4:1;
  K (Lys), G (Gly) and I (Ile) at a ratio of 1:4:1;
  D (Asp), G (Gly) and I (Ile) at a ratio of 1:4:1;
  E (Glu), G (Gly) and I (Ile) at a ratio of 1:4:1; or
  G (Gly), A (Ala) and F (Phe) at a ratio of 1:3:2;
ii) when the [hydrophobic EBP] is the elastin-based polypeptide block of SEQ ID NO: 2, each X of the repeating pentapeptide consists of:
  G (Gly), A (Ala) and F (Phe) at a ratio of 1:3:2;
  K (Lys), A (Ala) and F (Phe) at a ratio of 1:3:2;
  D (Asp), A (Ala) and F (Phe) at a ratio of 1:3:2;
  K (Lys) and F (Phe) at a ratio of 3:3;
  D (Asp) and F (Phe) at a ratio of 3:3;
  H (His), A (Ala) and I (Ile) at a ratio of 3:2:1;
  H (His) and G (Gly) at a ratio of 5:1; or
  G (Gly), C(Cys) and F (Phe) at a ratio of 1:3:2; and
iii) when the [hydrophobic EBP] is the elastin-based polypeptide block of SEQ ID NO: 3, each X of the repeating pentapeptide consists of:
  G (Gly), A (Ala) and F (Phe) at a ratio of 1:4:1; or
  G (Gly), A (Ala) and F (Phe) at a ratio of 1:3:2.

11. The triblock polypeptide with a temperature responsiveness according to claim 10, wherein when the [hydrophobic EBP] is a [VPGXG VPGXG VPGXG VPGXG VPGXG VPGXG] block of SEQ ID NO: 1, the [hydrophobic EBP] is SEQ ID NO: 23, SEQ ID NO: 25, SEQ ID NO: 27, SEQ ID NO: 29, or SEQ ID NO: 31.

12. The triblock polypeptide with a temperature responsiveness according to claim 10, wherein when the [hydrophobic EBP] is a [VPAXG VPAXG VPAXG VPAXG VPAXG VPAXG] block of SEQ ID NO: 2, the [hydrophobic EBP] is SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39.

13. The triblock polypeptide with a temperature responsiveness according to claim 10, wherein when the [hydrophobic EBP] is an [IPAXG IPAXG IPAXG IPAXG IPAXG IPAXG] block of SEQ ID NO: 3, the [hydrophobic EBP] is SEQ ID NO: 40 or SEQ ID NO: 41.

14. A hydrogel prepared by a process comprising:
applying a temperature, which is at or above the lower critical solution temperature of the [hydrophobic EBP], to the triblock polypeptide according claim 10, wherein the triblock polypeptide undergoes self-assembly and phase transition to form a physically crosslinked network.

15. The hydrogel according to claim 14, wherein the hydrogel undergoes reversible sol-gel or gel-sol transition in response to temperature.

16. The hydrogel according to claim 14, wherein the hydrogel has enhanced mechanical strength due to chemical crosslinkages between the tyrosine residues of the resilin-based polypeptide block.

17. A composition for drug delivery comprising the hydrogel according to claim 14.

18. A scaffold for tissue engineering comprising the hydrogel according to claim 14.

19. A kit for tissue or organ regeneration comprising the hydrogel according to claim 14.

\* \* \* \* \*

SEQUENCE LISTING

<160> NUMBER OF SEQ ID NOS: 55

<210> SEQ ID NO 1
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural

```
<400> SEQUENCE: 1

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural

<400> SEQUENCE: 2

Val Pro Ala Xaa Gly Val Pro Ala Xaa Gly Val Pro Ala Xaa Gly Val
1               5                   10                  15

Pro Ala Xaa Gly Val Pro Ala Xaa Gly Val Pro Ala Xaa Gly
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural

<400> SEQUENCE: 3

Ile Pro Ala Xaa Gly Ile Pro Ala Xaa Gly Ile Pro Ala Xaa Gly Ile
1               5                   10                  15

Pro Ala Xaa Gly Ile Pro Ala Xaa Gly Ile Pro Ala Xaa Gly
            20                  25                  30

<210> SEQ ID NO 4
<211> LENGTH: 90
<212> TYPE: DNA
<213> ORGANISM: Artificial Sequence
<220> FEATURE:
<223> OTHER INFORMATION: EBP

<400> SEQUENCE: 4
gtcccaggtg gaggtgtacc cggcgcgggt gtcccaggtg gaggtgtacc tgggggtggg      60
gtccctggta ttggcgtacc tggaggcggc                                      90

<210> SEQ ID NO 5
<211> LENGTH: 90
<212> TYPE: DNA
<213> ORGANISM: Artificial Sequence
<220> FEATURE:
<223> OTHER INFORMATION: EBP

<400> SEQUENCE: 5
gttccagctg gcggtgtacc tgctgctgct gttccggccg gtggtgttcc ggcgggcggc      60
gtgcctgcaa taggagttcc cgctggtggc                                      90

<210> SEQ ID NO 6
<211> LENGTH: 90
<212> TYPE: DNA
<213> ORGANISM: Artificial Sequence
<220> FEATURE:
<223> OTHER INFORMATION: EBP

<400> SEQUENCE: 6
```

```
gttccgggtg gtggtgttcc gggtaaaggt gttccgggtg gtggtgttcc gggtggtggt      60
ggtgttccgg gtatcggtgt tccgggtggc                                      90

<210> SEQ ID NO 7
<211> LENGTH: 90
<212> TYPE: DNA
<213> ORGANISM: Artificial Sequence
<220> FEATURE:
<223> OTHER INFORMATION: EBP

<400> SEQUENCE: 7
gttccggcgg gtggtgttcc ggcgaaaggt gttccggcgg gtggtgttcc ggcgggtggt      60
gttccggcga tcggtgttcc ggcgggtggc                                      90

<210> SEQ ID NO 8
<211> LENGTH: 90
<212> TYPE: DNA
<213> ORGANISM: Artificial Sequence
<220> FEATURE:
<223> OTHER INFORMATION: EBP

<400> SEQUENCE: 8
gttccgggtg gtggtgttcc gggtgatggt gttccgggtg gtggtgttcc gggtggtggt      60
ggtgttccgg gtatcggtgt tccgggtggc                                      90

<210> SEQ ID NO 9
<211> LENGTH: 90
<212> TYPE: DNA
<213> ORGANISM: Artificial Sequence
<220> FEATURE:
<223> OTHER INFORMATION: EBP

<400> SEQUENCE: 9
gttccggcgg gtggtgttcc ggcggatggt gttccggcgg gtggtgttcc ggcgggtggt      60
gttccggcga tcggtgttcc ggcgggtggc                                      90

<210> SEQ ID NO 10
<211> LENGTH: 90
<212> TYPE: DNA
<213> ORGANISM: Artificial Sequence
<220> FEATURE:
<223> OTHER INFORMATION: EBP

<400> SEQUENCE: 10
gttccgggtg gtggtgttcc gggtgaaggt gttccgggtg gtggtgttcc gggtggtggt      60
ggtgttccgg gtatcggtgt tccgggtggc                                      90

<210> SEQ ID NO 11
<211> LENGTH: 90
<212> TYPE: DNA
<213> ORGANISM: Artificial Sequence
<220> FEATURE:
<223> OTHER INFORMATION: EBP

<400> SEQUENCE: 11
gttccggcgg gtggtgttcc ggcggaaggt gttccggcgg gtggtgttcc ggcgggtggt      60
gttccggcga tcggtgttcc ggcgggtggc                                      90

<210> SEQ ID NO 12
<211> LENGTH: 90
<212> TYPE: DNA
```

```
<213> ORGANISM: Artificial Sequence
<220> FEATURE:
<223> OTHER INFORMATION: EBP

<400> SEQUENCE: 12
gtcccgggtg cgggcgtgcc gggatttgga gttccgggtg cgggtgttcc aggcggtggt      60
gttccgggcg cgggcgtgcc gggcttttggc                                     90

<210> SEQ ID NO 13
<211> LENGTH: 90
<212> TYPE: DNA
<213> ORGANISM: Artificial Sequence
<220> FEATURE:
<223> OTHER INFORMATION: EBP

<400> SEQUENCE: 13
gtgccggcgg cgggcgttcc agcctttggt gtgccagcgg cgggagttcc ggccggtggc      60
gtgccggcag cgggcgtgcc ggcttttggc                                      90

<210> SEQ ID NO 14
<211> LENGTH: 90
<212> TYPE: DNA
<213> ORGANISM: Artificial Sequence
<220> FEATURE:
<223> OTHER INFORMATION: EBP

<400> SEQUENCE: 14
gtgccggcgg cgggcgttcc agcctttggt gtgccagcgg cgggagttcc ggccaaaggc      60
gtgccggcag cgggcgtgcc ggcttttggc                                      90

<210> SEQ ID NO 15
<211> LENGTH: 90
<212> TYPE: DNA
<213> ORGANISM: Artificial Sequence
<220> FEATURE:
<223> OTHER INFORMATION: EBP

<400> SEQUENCE: 15
gtgccggcgg cgggcgttcc agcctttggt gtgccagcgg cgggagttcc ggccgatggc      60
gtgccggcag cgggcgtgcc ggcttttggc                                      90

<210> SEQ ID NO 16
<211> LENGTH: 90
<212> TYPE: DNA
<213> ORGANISM: Artificial Sequence
<220> FEATURE:
<223> OTHER INFORMATION: EBP

<400> SEQUENCE: 16
gttccagcgt ttggcgtgcc agcgaaaggt gttccggcgt tggggttcc cgcgaaaggt      60 gtgccggcct ttggtgtgcc ggccaaaggc                                      90

<210> SEQ ID NO 17
<211> LENGTH: 90
<212> TYPE: DNA
<213> ORGANISM: Artificial Sequence
<220> FEATURE:
<223> OTHER INFORMATION: EBP

<400> SEQUENCE: 17
gttccagcgt ttggcgtgcc agcggatggt gttccggcgt tggggttcc cgcggatggt      60 gtgccggcct ttggtgtgcc ggccgatggc                                      90
```

<210> SEQ ID NO 18
<211> LENGTH: 90
<212> TYPE: DNA
<213> ORGANISM: Artificial Sequence
<220> FEATURE:
<223> OTHER INFORMATION: EBP

<400> SEQUENCE: 18
gtgccggcgc atggagttcc tgccgccggt gttcctgcgc atggtgtacc ggcaattggc    60
gttccggcac atggtgtgcc ggccgccggc    90

<210> SEQ ID NO 19
<211> LENGTH: 90
<212> TYPE: DNA
<213> ORGANISM: Artificial Sequence
<220> FEATURE:
<223> OTHER INFORMATION: EBP

<400> SEQUENCE: 19
gttccggccg gaggtgtacc ggcgcatggt gttccggcac atggtgtgcc ggctcacggt    60
gtgcctgcgc atggcgttcc tgcgcatggc    90

<210> SEQ ID NO 20
<211> LENGTH: 90
<212> TYPE: DNA
<213> ORGANISM: Artificial Sequence
<220> FEATURE:
<223> OTHER INFORMATION: EBP

<400> SEQUENCE: 20
gtgccggcgt gcggcgttcc agcctttggt gtgccagcgt gcggagttcc ggccggtggc    60
gtgccggcat gcggcgtgcc ggcttttggc    90

<210> SEQ ID NO 21
<211> LENGTH: 90
<212> TYPE: DNA
<213> ORGANISM: Artificial Sequence
<220> FEATURE:
<223> OTHER INFORMATION: EBP

<400> SEQUENCE: 21
attcctgcag ccggtatccc ggccggtggc attccggcag ccggcattcc ggccgccggc    60
atcccggcat ttggcattcc tgcagcaggc    90

<210> SEQ ID NO 22
<211> LENGTH: 90
<212> TYPE: DNA
<213> ORGANISM: Artificial Sequence
<220> FEATURE:
<223> OTHER INFORMATION: EBP

<400> SEQUENCE: 22
attccggccg caggcattcc tgcatttggt attccggcgg caggcattcc tgccggtggc    60
atcccggcag cgggcattcc ggcctttggc    90

<210> SEQ ID NO 23
<211> LENGTH: 30
<212> TYPE: PRT
<213> ORGANISM: Artificial Sequence
<220> FEATURE:
<223> OTHER INFORMATION: EBP -continued

```
<400> SEQUENCE: 23

Val Pro Gly Gly Gly Val Pro Ala Gly Val Pro Gly Gly Gly Val
1               5                   10                  15

Pro Gly Gly Gly Val Pro Gly Ile Gly Val Pro Gly Gly Gly
                20                  25                  30

<210> SEQ ID NO 24
<211> LENGTH: 30
<212> TYPE: PRT
<213> ORGANISM: Artificial Sequence
<220> FEATURE:
<223> OTHER INFORMATION: EBP

<400> SEQUENCE: 24

Val Pro Ala Gly Gly Val Pro Ala Ala Gly Val Pro Ala Gly Gly Val
1               5                   10                  15

Pro Ala Gly Gly Val Pro Ala Ile Gly Val Pro Ala Gly Gly
                20                  25                  30

<210> SEQ ID NO 25
<211> LENGTH: 30
<212> TYPE: PRT
<213> ORGANISM: Artificial Sequence
<220> FEATURE:
<223> OTHER INFORMATION: EBP

<400> SEQUENCE: 25

Val Pro Gly Gly Gly Val Pro Gly Lys Gly Val Pro Gly Gly Val
1               5                   10                  15

Pro Gly Gly Gly Val Pro Gly Ile Gly Val Pro Gly Gly Gly
                20                  25                  30

<210> SEQ ID NO 26
<211> LENGTH: 30
<212> TYPE: PRT
<213> ORGANISM: Artificial Sequence
<220> FEATURE:
<223> OTHER INFORMATION: EBP

<400> SEQUENCE: 26

Val Pro Ala Gly Gly Val Pro Ala Lys Gly Val Pro Ala Gly Gly Val
1               5                   10                  15

Pro Ala Gly Gly Val Pro Ala Ile Gly Val Pro Ala Gly Gly
                20                  25                  30

<210> SEQ ID NO 27
<211> LENGTH: 30
<212> TYPE: PRT
<213> ORGANISM: Artificial Sequence
<220> FEATURE:
<223> OTHER INFORMATION: EBP

<400> SEQUENCE: 27

Val Pro Gly Gly Gly Val Pro Gly Asp Gly Val Pro Gly Gly Gly Val
1               5                   10                  15

Pro Gly Gly Gly Val Pro Gly Ile Gly Val Pro Gly Gly Gly
                20                  25                  30

<210> SEQ ID NO 28
<211> LENGTH: 30
<212> TYPE: PRT
<213> ORGANISM: Artificial Sequence
<220> FEATURE:
<223> OTHER INFORMATION: EBP
```

<400> SEQUENCE: 28

Val Pro Ala Gly Gly Val Pro Ala Asp Gly Val Pro Ala Gly Gly Val
1               5                   10                  15

Pro Ala Gly Gly Val Pro Ala Ile Gly Val Pro Ala Gly Gly
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: EBP

<400> SEQUENCE: 29

Val Pro Gly Gly Gly Val Pro Gly Glu Gly Val Pro Gly Gly Gly Val
1               5                   10                  15

Pro Gly Gly Gly Val Pro Gly Ile Gly Val Pro Gly Gly Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: EBP

<400> SEQUENCE: 30

Val Pro Ala Gly Gly Val Pro Ala Glu Gly Val Pro Ala Gly Gly Val
1               5                   10                  15

Pro Ala Gly Gly Val Pro Ala Ile Gly Val Pro Ala Gly Gly
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: EBP

<400> SEQUENCE: 31

Val Pro Gly Ala Gly Val Pro Gly Phe Gly Val Pro Gly Ala Gly Val
1               5                   10                  15

Pro Gly Gly Gly Val Pro Gly Ala Gly Val Pro Gly Phe Gly
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: EBP

<400> SEQUENCE: 32

Val Pro Ala Ala Gly Val Pro Ala Phe Gly Val Pro Ala Ala Gly Val
1               5                   10                  15

Pro Ala Gly Gly Val Pro Ala Ala Gly Val Pro Ala Phe Gly
            20                  25                  30

<210> SEQ ID NO 33
<211> LENGTH: 30
<212> TYPE: PRT
<213> ORGANISM: Artificial Sequence
<220> FEATURE:

```
<223> OTHER INFORMATION: EBP

<400> SEQUENCE: 33

Val Pro Ala Ala Gly Val Pro Ala Phe Gly Val Pro Ala Ala Gly Val
1               5                   10                  15
Pro Ala Lys Gly Val Pro Ala Ala Gly Val Pro Ala Phe Gly
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: EBP

<400> SEQUENCE: 34

Val Pro Ala Ala Gly Val Pro Ala Phe Gly Val Pro Ala Ala Gly Val
1               5                   10                  15
Pro Ala Asp Gly Val Pro Ala Ala Gly Val Pro Ala Phe Gly
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: EBP

<400> SEQUENCE: 35

Val Pro Ala Phe Gly Val Pro Ala Lys Gly Val Pro Ala Phe Gly Val
1               5                   10                  15
Pro Ala Lys Gly Val Pro Ala Phe Gly Val Pro Ala Lys Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: EBP

<400> SEQUENCE: 36

Val Pro Ala Phe Gly Val Pro Ala Asp Gly Val Pro Ala Phe Gly Val
1               5                   10                  15
Pro Ala Asp Gly Val Pro Ala Phe Gly Val Pro Ala Asp Gly
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: EBP

<400> SEQUENCE: 37

Val Pro Ala His Gly Val Pro Ala Ala Gly Val Pro Ala His Gly Val
1               5                   10                  15
Pro Ala Ile Gly Val Pro Ala His Gly Val Pro Ala Ala Gly
            20                  25                  30

<210> SEQ ID NO 38
<211> LENGTH: 30
<212> TYPE: PRT
<213> ORGANISM: Artificial Sequence
```

```
<220> FEATURE:
<223> OTHER INFORMATION: EBP

<400> SEQUENCE: 38

Val Pro Ala Gly Gly Val Pro Ala His Gly Val Pro Ala His Gly Val
1               5                   10                  15

Pro Ala His Gly Val Pro Ala His Gly Val Pro Ala His Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: EBP

<400> SEQUENCE: 39

Val Pro Ala Cys Gly Val Pro Ala Phe Gly Val Pro Ala Cys Gly Val
1               5                   10                  15

Pro Ala Gly Gly Val Pro Ala Cys Gly Val Pro Ala Phe Gly
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: EBP

<400> SEQUENCE: 40

Ile Pro Ala Ala Gly Ile Pro Ala Gly Gly Ile Pro Ala Ala Gly Ile
1               5                   10                  15

Pro Ala Ala Gly Ile Pro Ala Phe Gly Ile Pro Ala Ala Gly
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: EBP

<400> SEQUENCE: 41

Ile Pro Ala Ala Gly Ile Pro Ala Phe Gly Ile Pro Ala Ala Gly Ile
1               5                   10                  15

Pro Ala Gly Gly Ile Pro Ala Ala Gly Ile Pro Ala Phe Gly
            20                  25                  30

<210> SEQ ID NO 42
<211> LENGTH: 90
<212> TYPE: DNA
<213> ORGANISM: Artificial Sequence
<220> FEATURE:
<223> OTHER INFORMATION: RBP[m-Dros]1

<400> SEQUENCE: 42
ggcggccgtc cgtcagattc ttatggcgca ccgggtgggg gtaatggcgg ccgtccatct    60
tcgagctatg cgcaccggg ccaaggtaat                                      90

<210> SEQ ID NO 43
<211> LENGTH: 90
<212> TYPE: DNA
<213> ORGANISM: Artificial Sequence
<220> FEATURE:
```

<223> OTHER INFORMATION: RBP[Dros]1

<400> SEQUENCE: 43
ggggcgccgg gtggtggcaa cggtggtcgt ccgagcgata cctacggggc gccgggtggt        60
ggcaacggtg gtcgtccgag cgatacctac        90

<210> SEQ ID NO 44
<211> LENGTH: 30
<212> TYPE: PRT
<213> ORGANISM: Artificial Sequence
<220> FEATURE:
<223> OTHER INFORMATION: RBP[m-Dros]1

<400> SEQUENCE: 44

Gly Gly Arg Pro Ser Asp Ser Tyr Gly Ala Pro Gly Gly Gly Asn Gly
1               5                   10                  15

Gly Arg Pro Ser Ser Ser Tyr Gly Ala Pro Gly Gln Gly Asn
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: RBP[Dros]1

<400> SEQUENCE: 45

Gly Gly Arg Pro Ser Asp Thr Tyr Gly Ala Pro Gly Gly Gly Asn Gly
1               5                   10                  15

Gly Arg Pro Ser Asp Thr Tyr Gly Ala Pro Gly Gly Gly Asn
            20                  25                  30

<210> SEQ ID NO 46
<211> LENGTH: 5
<212> TYPE: PRT
<213> ORGANISM: Artificial Sequence
<220> FEATURE:
<223> OTHER INFORMATION: Elastin-based peptide, Xaa can be any amino
      acid, natural or non-natural

<400> SEQUENCE: 46

Val Pro Gly Xaa Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Elastin-based peptide, Xaa can be any amino
      acid, natural or non-natural

<400> SEQUENCE: 47

Val Pro Ala Xaa Gly
1               5

<210> SEQ ID NO 48
<211> LENGTH: 15
<212> TYPE: PRT
<213> ORGANISM: Artificial Sequence
<220> FEATURE:
<223> OTHER INFORMATION: rec1-resilin

<400> SEQUENCE: 48

Gly Gly Arg Pro Ser Asp Ser Tyr Gly Ala Pro Gly Gly Gly Asn

<210> SEQ ID NO 49
<211> LENGTH: 5
<212> TYPE: PRT
<213> ORGANISM: Artificial Sequence
<220> FEATURE:
<223> OTHER INFORMATION: Elastin-based peptide, Xaa can be any amino
    acid, natural or non-natural

<400> SEQUENCE: 49

Ile Pro Ala Xaa Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Elastin-based peptide

<400> SEQUENCE: 50

Val Pro Gly Val Gly
1               5

<210> SEQ ID NO 51
<211> LENGTH: 64
<212> TYPE: DNA
<213> ORGANISM: Artificial Sequence
<220> FEATURE:
<223> OTHER INFORMATION: oligonucleotide having XbaI compatible sticky
    end

<400> SEQUENCE: 51
ctagaaataa tttttaact ttaagaagga ggagtacata tgggctactg ataatgatct    60
tcag                                                               64

<210> SEQ ID NO 52
<211> LENGTH: 66
<212> TYPE: DNA
<213> ORGANISM: Artificial Sequence
<220> FEATURE:
<223> OTHER INFORMATION: oligonucleotide having BamHI compatible sticky
    end

<400> SEQUENCE: 52
gatcctgaag atcattatca gtagcccata tgtactcctc cttcttaaag ttaaacaaaa    60
ttattt                                                               66

<210> SEQ ID NO 53
<211> LENGTH: 15
<212> TYPE: PRT
<213> ORGANISM: Artificial Sequence
<220> FEATURE:
<223> OTHER INFORMATION: Repeat sequence in RBP

<400> SEQUENCE: 53

Gly Gly Arg Pro Ser Asp Thr Tyr Gly Ala Pro Gly Gly Gly Asn
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: modified repeat sequence in RBP

```
<400> SEQUENCE: 54

Gly Gly Arg Pro Ser Asp Ser Tyr Gly Ala Pro Gly Gly Gly Asn
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: modified repeat sequence in RBP

<400> SEQUENCE: 55

Gly Gly Arg Pro Ser Ser Ser Tyr Gly Ala Pro Gly Gln Gly Asn
1               5                   10                  15
```